United States Patent
Orwar et al.

(10) Patent No.: US 9,658,240 B2
(45) Date of Patent: May 23, 2017

(54) MICROFLUIDIC DEVICE WITH HOLDING INTERFACE, AND METHODS OF USE

(71) Applicant: Fluicell AB, Göteborg (SE)

(72) Inventors: Owe Orwar, Hovas (SE); Alar Ainla, Göteborg (SE); Aldo Jesorka, Göteborg (SE); Gavin Jeffries, Göteborg (SE)

(73) Assignee: Fluicell AB, Göteborg (SE)

( * ) Notice: Subject to any disclaimer, the term of this patent is extended or adjusted under 35 U.S.C. 154(b) by 517 days.

(21) Appl. No.: 14/072,153

(22) Filed: Nov. 5, 2013

(65) Prior Publication Data

US 2014/0147930 A1    May 29, 2014

Related U.S. Application Data

(63) Continuation of application No. PCT/IB2012/001047, filed on May 7, 2012.
(Continued)

(51) Int. Cl.
*G01N 35/00* (2006.01)
*G01N 35/10* (2006.01)
(Continued)

(52) U.S. Cl.
CPC .......... *G01N 35/1072* (2013.01); *B01L 3/021* (2013.01); *B01L 3/022* (2013.01);
(Continued)

(58) Field of Classification Search
CPC ................................................ G01N 35/1072
(Continued)

(56) References Cited

U.S. PATENT DOCUMENTS

| 5,726,404 | A | 3/1998 | Brody |
| 6,407,437 | B1* | 6/2002 | Burger ................ B01L 3/021 |
| | | | 257/414 |
| 7,314,595 | B2 | 1/2008 | Honkanen et al. |
| 7,740,472 | B2 | 6/2010 | Delamarche et al. |

(Continued)

FOREIGN PATENT DOCUMENTS

| EP | 1366820 A1 | 12/2003 | |
| GB | WO 2010061201 A2 * | 6/2010 | ........ B01L 3/502715 |

(Continued)

OTHER PUBLICATIONS

EPO Patent Translation of JP 08290377 (A) specification.*
(Continued)

*Primary Examiner* — Christopher A Hixson
*Assistant Examiner* — Emily Berkeley
(74) *Attorney, Agent, or Firm* — Saul Ewing LLP; Brian R. Landry

(57) ABSTRACT

Aspects of the present invention provide a freestanding microfluidic pipette with integrated wells for solution storage. Further aspects of the invention provide a holding interface to provide connectivity with external control components. One aspect of the invention provides a system for applying a microfluidic device in microscopy. The system includes: a microfluidic device having an elongated shape and defining one or more wells for solution storage and processing; and an interface adapted and configured to hold the microfluidic device in a freestanding manner and facilitate simultaneous connection of the one or more wells with a flow controller. Another aspect of the invention provides a method for utilizing a microfluidic device. The method includes: providing a device as described herein; positioning the device adjacent to a microscope; and actuating the interface to operate the microfluidic device.

20 Claims, 24 Drawing Sheets

Related U.S. Application Data

(60) Provisional application No. 61/483,468, filed on May 6, 2011.

(51) Int. Cl.
 *B01L 3/02* (2006.01)
 *B01L 3/00* (2006.01)

(52) U.S. Cl.
 CPC ....... *B01L 3/5027* (2013.01); *B01L 3/502715* (2013.01); *B01L 2300/0861* (2013.01); *B01L 2400/0487* (2013.01); *Y10T 436/25* (2015.01)

(58) Field of Classification Search
 USPC .......................................................... 436/174
 See application file for complete search history.

(56) References Cited

U.S. PATENT DOCUMENTS

| | | | |
|---|---|---|---|
| 2005/0247673 | A1 | 11/2005 | Delamarche et al. |
| 2006/0093697 | A1* | 5/2006 | Delamarche .......... B01L 3/0262 425/375 |
| 2006/0127579 | A1 | 6/2006 | Delamarche et al. |
| 2006/0234298 | A1 | 10/2006 | Chiu et al. |
| 2007/0231458 | A1* | 10/2007 | Gale .................... B01J 19/0046 427/2.11 |
| 2010/0187452 | A1* | 7/2010 | Mukaddam ............. B01L 3/021 251/61.1 |

FOREIGN PATENT DOCUMENTS

| | | | | |
|---|---|---|---|---|
| JP | 08290377 | A | * 11/1996 | |
| JP | 8290377 | A | 11/1996 | |
| WO | WO 0212734 | A1 | * 2/2002 | ........ B01L 3/502738 |
| WO | 03068906 | A1 | 8/2003 | |
| WO | WO 03/068906 | A1 | 8/2003 | |
| WO | 2004034185 | A2 | 4/2004 | |
| WO | WO 2004034185 | A2 | 4/2004 | |
| WO | 2006014460 | A2 | 9/2006 | |
| WO | WO 2008002483 | A2 | * 1/2008 | ........ B01L 3/502738 |
| WO | 2010128483 | A2 | 11/2010 | |
| WO | WO 2010128483 | A2 | 11/2010 | |
| WO | 2011067670 | A2 | 12/2011 | |

OTHER PUBLICATIONS

International Search Report for International Application PCT/IB2012/001047 mailed Mar. 28, 2013.

Written Opinion for International Application PCT/IB2012/001047 mailed Nov. 6, 2013.

International Preliminary Report on Patentability for International Application PCT/IB2012/001047 mailed Nov. 21, 2013.

Ainla et al., "A Microfluidic Pipette for Single-Cell Pharmacology," Analytical Chemistry, vol. 82, No. 11, pp. 4529-4536, Jun. 1, 2010.

Chen, et al., "The Chemistrode: A Droplet-based Microfluidic Device for Stimulation and Recording With High Temporal, Spatial, and Chemical Resolution," PNAS, vol. 105, No. 44, pp. 16843-16848, Nov. 4, 2008.

Juncker, et al., "Multipurposed Microfluidic Probe," Nature materials, vol. 4, pp. 622-628, Aug. 2005.

Feinerman, et al., "A Picoliter 'fountain-pen' Using Co-axial Dual Pipettes," Journal of Neuroscience Methods, 127, pp. 75-84, Apr. 22, 2003.

Lovchik, et al., "Multilayered Microfluidic Probe Heads," Journal of Micromechanics and Microengineering, 115006 (8pp) 19, Sep. 29, 2009.

Queval, et al, "Chamber and Microfluidic Probe for Microperfusion of Organotypic Brain Slices," Royal Society of Chemistry, Lab on a Chip, 10 pp. 326-334, Nov. 19, 2009.

Communication under Rule 164(2)(a) EPC, EP Patent Application No. 12 743 210.2, Jul. 5, 2016.

Chen, C. F., et al., "High-pressure needle interface for thermoplastic microfluidics", Lab Chip, 9, 50-55, 2009.

Cooksey, G. A., et al., "A vacuum manifold for rapid world-to-chip connectivity of complex PDMS microdevices", Lab Chip, 9, 1298-1300, 2009.

Fredrickson, C. K. et al., "Macro-to-micro interfaces for microfluidic devices", Lab Chip, 4, 526-533, 2004.

Ainla, A., et al., "A Microfluidic Pipette for Single-Cell Pharmacology", Anal. Chem. 82, 4529-4536, 2010.

Chen, D., et al., "The chemistrode: A droplet-based microfluidic device for stimulation and recording with high temporal, spatial, and chemical resolution", PNAS, 105(44), 16843-16848, 2008.

Feinerman, O., et al., "A picoliter 'fountain-pen' using co-axial dual pipettes", Journal of Neuroscience Methods, 127, 75-84, 2003.

Juncker, D., et al., "Multipurpose microfluidic probe", Nature Materials, 4, 622-628, 2005.

Lovchik, R. D., et al., "Multilayered microfluidic probe heads", J. Micromech. Microeng. 19, 1-8, 2009.

Queval, A., et al., "Chamber and microfluidic probe for microperfusion of organotypic brain slices", Lab Chip, 10, 326-334, 2010.

* cited by examiner

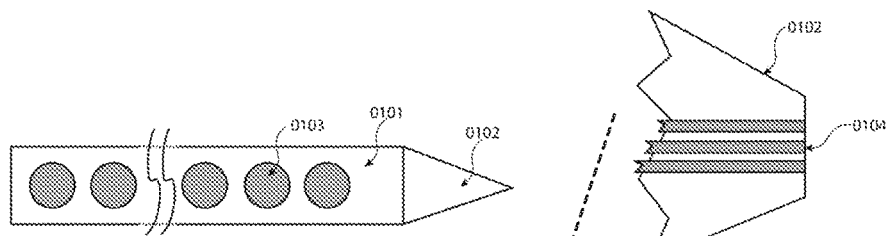
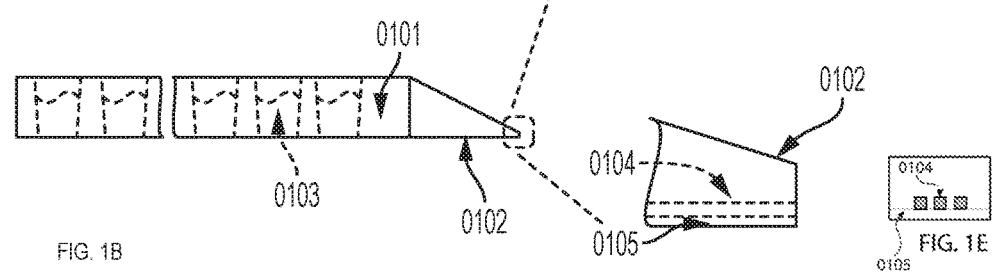
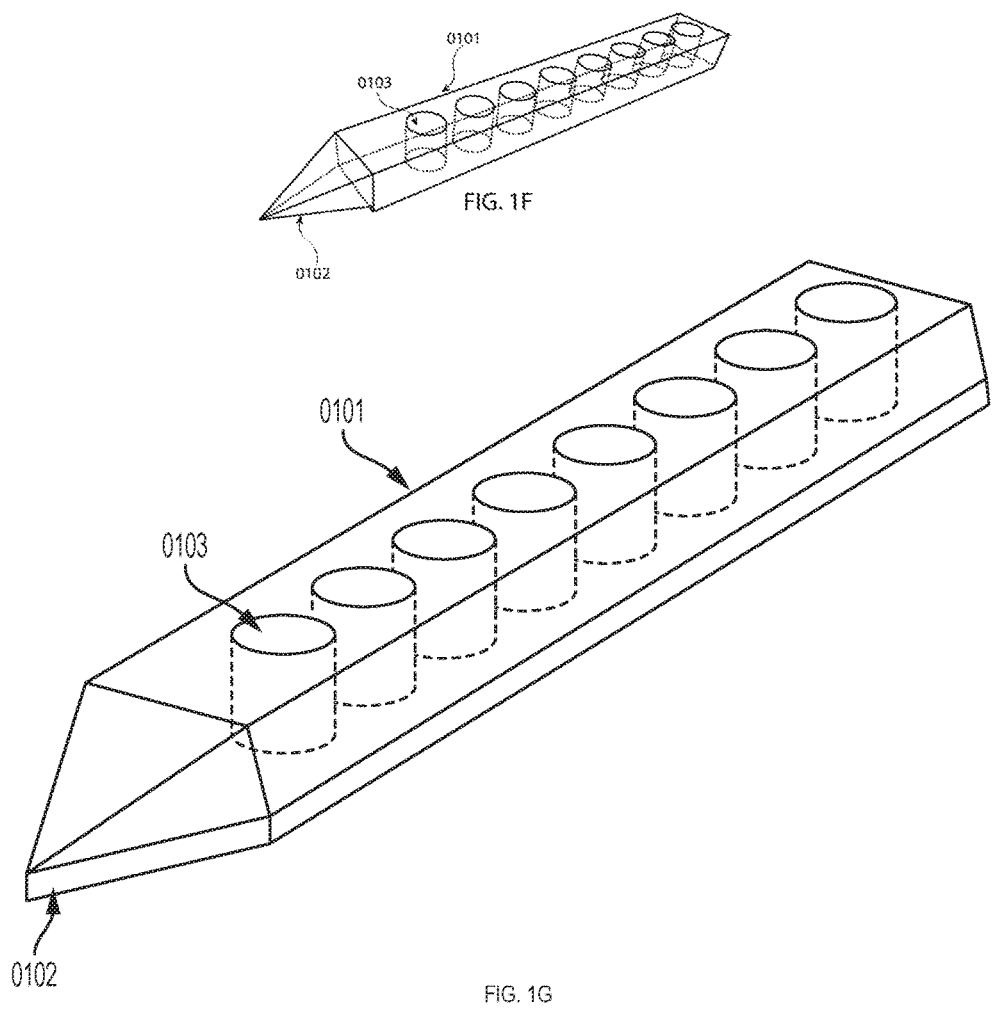

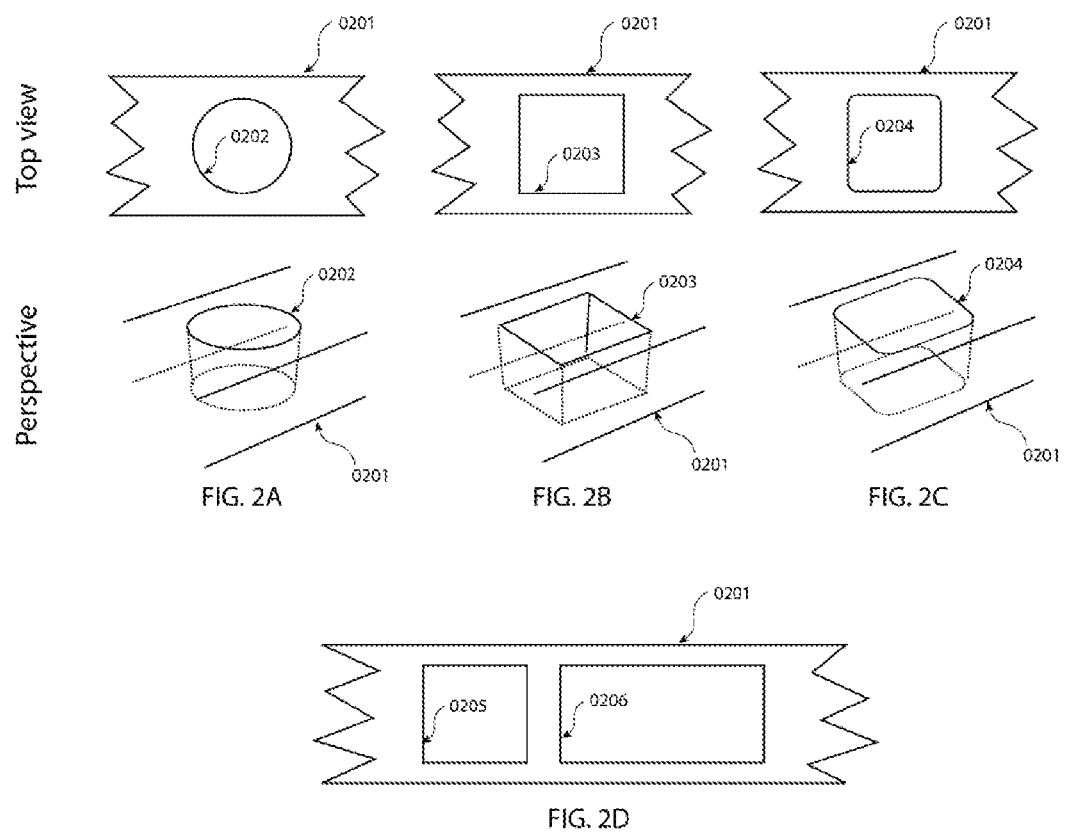

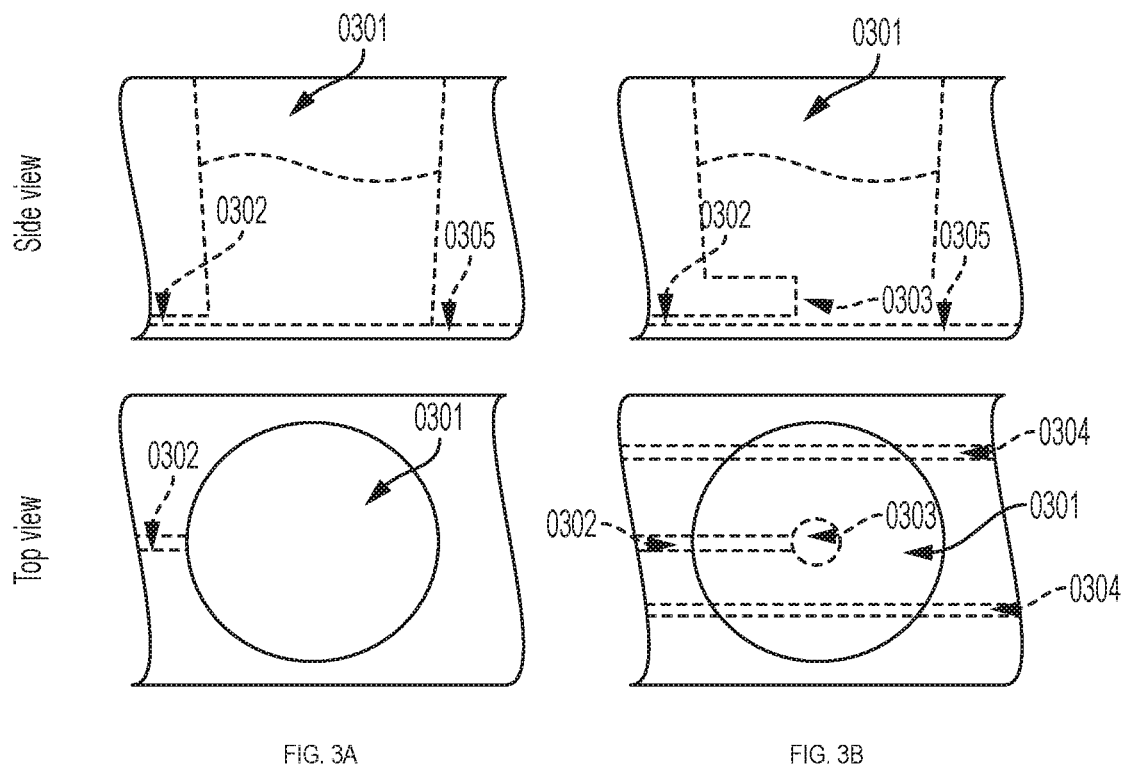
FIG. 3A   FIG. 3B
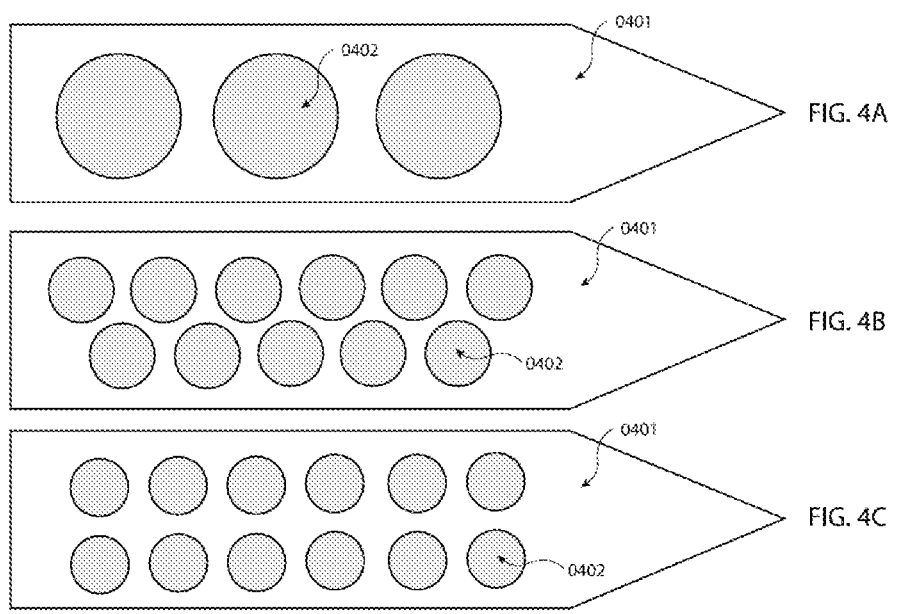
FIG. 4A
FIG. 4B
FIG. 4C

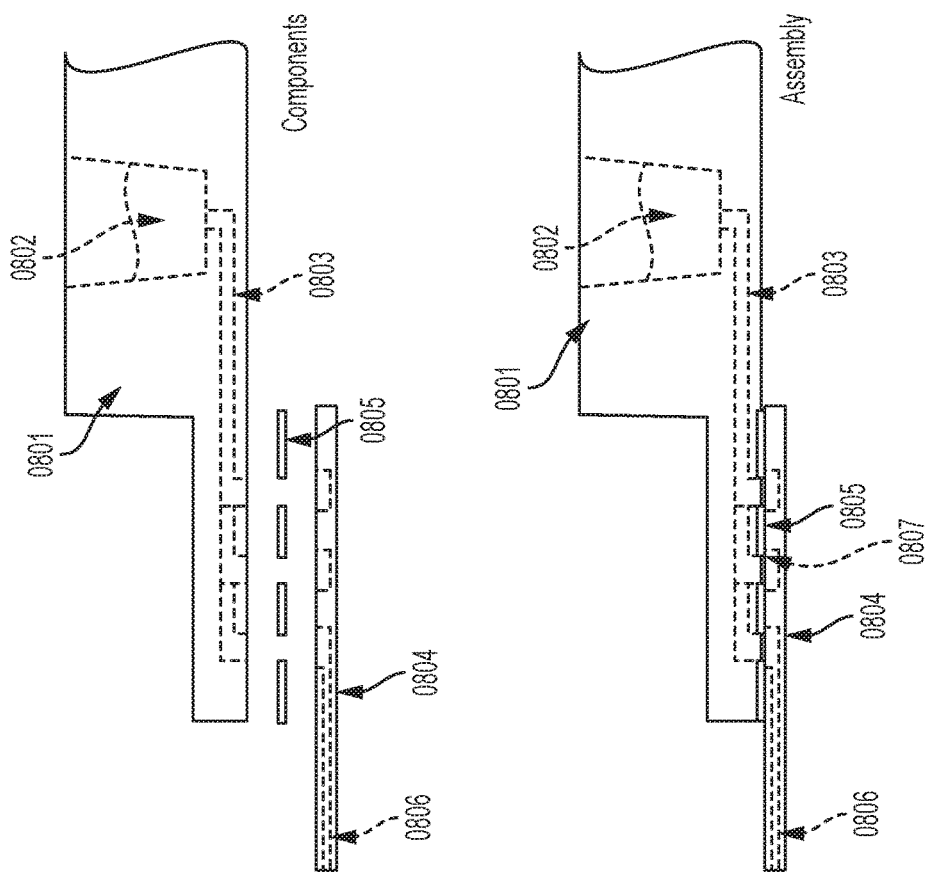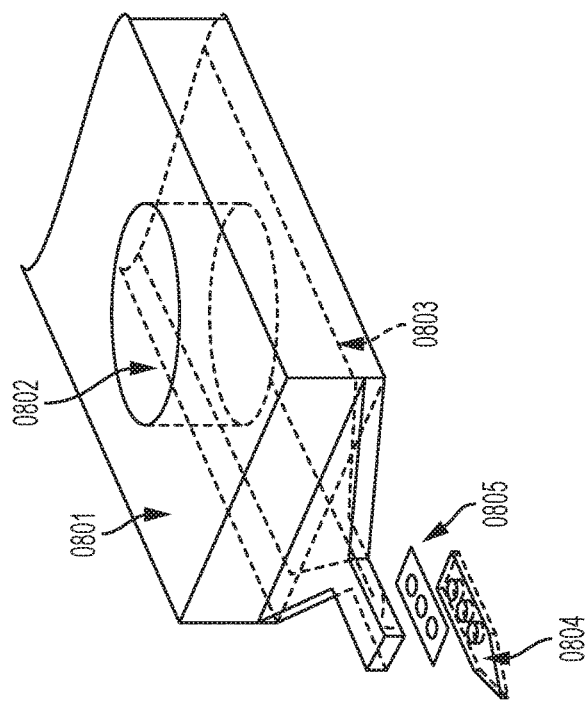
FIG. 8

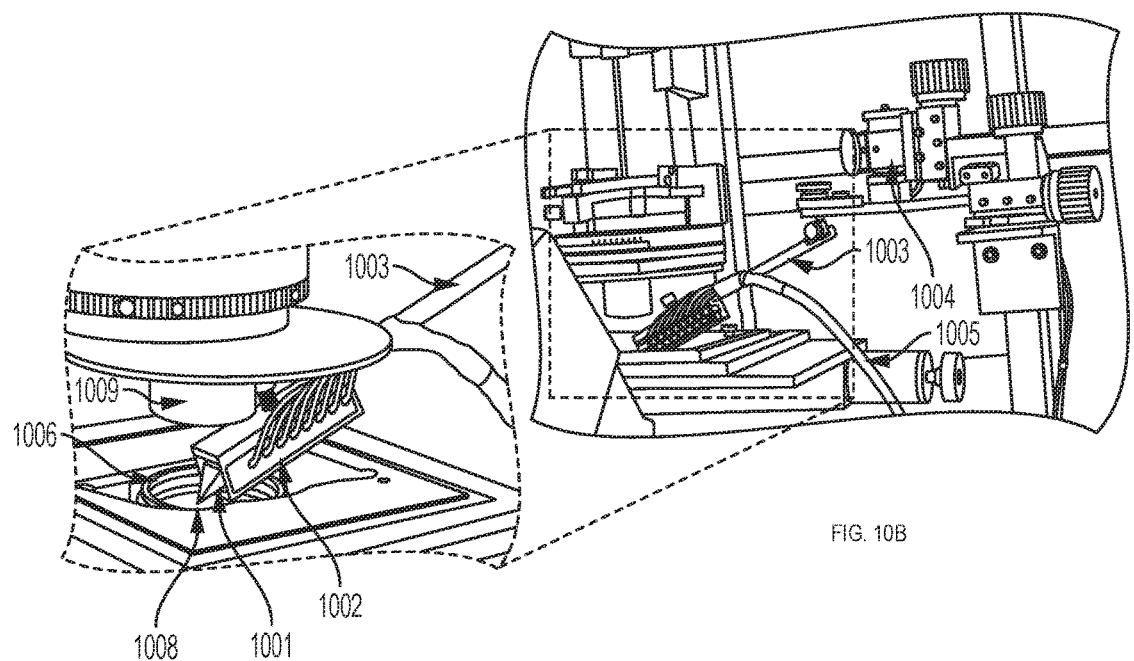
FIG. 10B
FIG. 10A
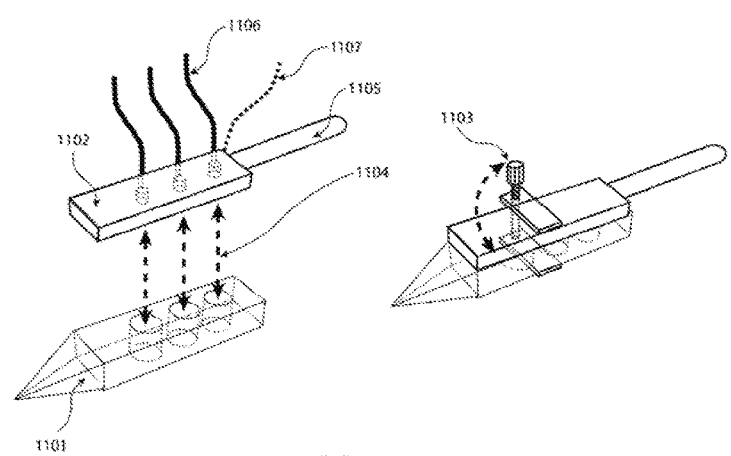
FIG. 11

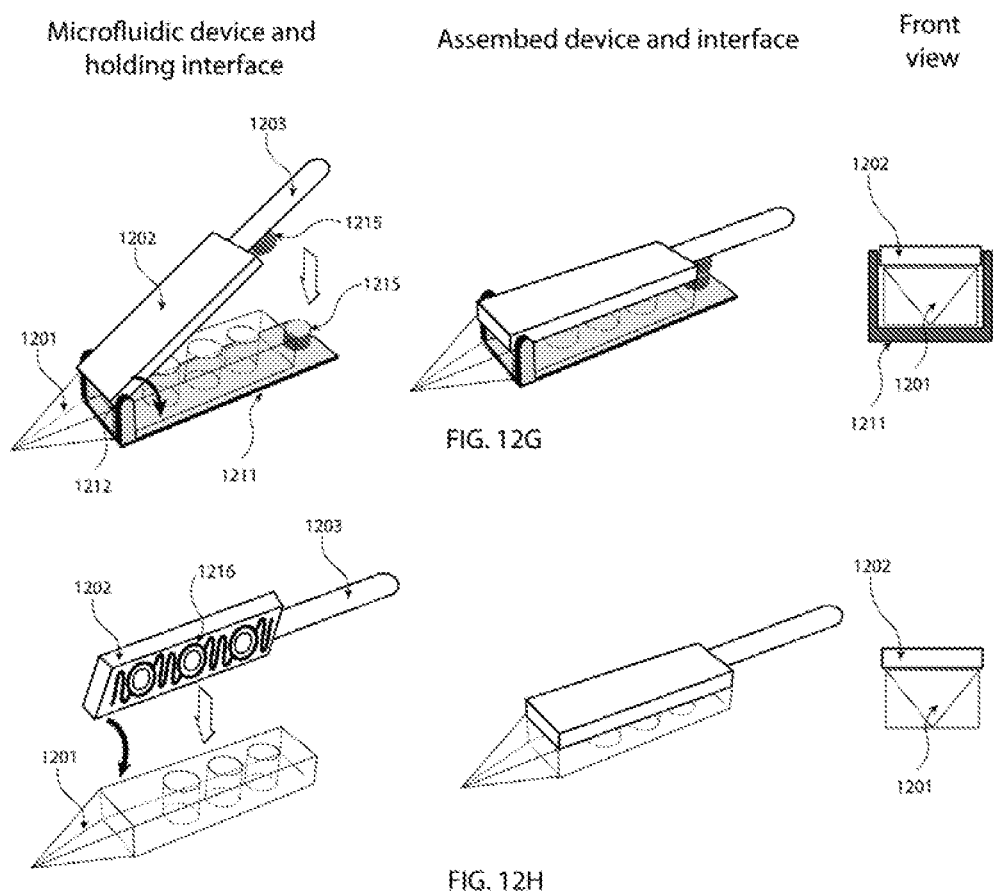

MICROFLUIDIC DEVICE WITH HOLDING INTERFACE, AND METHODS OF USE

CROSS-REFERENCE TO RELATED APPLICATIONS

This application is a continuation under 35 U.S.C. §120 of International Application No. PCT/IB2012/001047, which claims priority to U.S. Provisional Patent Application Ser. No. 61/483,468, filed May 6, 2011. This application is related to, but does not claim priority from, International Application No. PCT/US10/58926, filed Dec. 3, 2010 and published as International Publication No. WO 2011/067670 on Jun. 9, 2011, which claims priority to U.S. Provisional Patent Application Ser. No. 61/266,255, filed Dec. 3, 2009. The entire contents of each of these patent applications are hereby incorporated by reference herein.

BACKGROUND OF THE INVENTION

Microfluidic devices have found use in medicine, chemistry and biology, both as analytical monitoring and research tools. Microfluidics feature useful properties, such as low fabrication cost, very low reagent and analyte consumption, fast and controlled mixing, the possibility of fast solution switching and generation and maintaining of chemical gradients etc. Further, microchannels are well suited to address and analyze individual cells, as they can be made on a similar size scale.

Most microfluidic devices handle cells by using pressure or electrical field driven flow, acoustics or optical forces to capture and handle suspended cells from the flow. These devices, however, are not well suited to handle adherent cells, cell cultures such as organotypic tissues or native tissue slices, where cells cannot be transported by flow. Presently, common perfusion tools used in tissue experiments allow poor localization and have large solution consumption.

SUMMARY OF THE INVENTION

One aspect of the invention provides a system for applying a microfluidic device in microscopy. The system includes: a microfluidic device having an elongated shape and defining one or more wells for solution storage and processing; and an interface adapted and configured to hold the microfluidic device in a freestanding manner and facilitate simultaneous connection of the one or more wells with a flow controller.

This aspect of the invention can have a variety of embodiments. The interface can be coupled to a positioning device. The microfluidic device can be between about 6 mm and about 12 mm wide. The microfluidic device can be between about 3 mm and about 6 mm high. The microfluidic device can be between about 40 mm and about 80 mm long.

The microfluidic device can have a sharp protrusive tip, where one or more channels exits are positioned at the tip. The microfluidic device tip can have a pyramidal shape. The microfluidic device tip can have a flat triangular shape. The microfluidic device tip can have a flat rectangular shape. The microfluidic device can be made of optically transparent material close to tip.

The microfluidic device can have circular wells. The microfluidic device can have rectangular wells. The microfluidic device can have rectangular wells with rounded corners. The microfluidic device can have tapered wells. The wells of the microfluidic device can be of equal size. The wells of the microfluidic device can be of different sizes. The wells of the microfluidic device can have a volume between about 10 µL and about 50 µL. The wells of the microfluidic device can have a volume between about 50 µL and about 100 µL. The wells of the microfluidic device can have a volume between about 100 µL and about 500 µL.

The microfluidic device can have between 2 and 10 wells. The microfluidic device can have 8 wells.

A well-to-well separation distance in the microfluidic device can be between about 4 mm and about 12 mm. The well-to-well separation distance can be about 6 mm. The well-to-well separation distance can be about 9 mm. The well-to-well separation distance can be about 4.5 mm.

One or more microfluidic channels can be in direct fluid communication with one or more wells. A channel can be connected with a well through an orifice that is smaller in diameter than a bottom diameter of the well.

The wells in the microfluidic chip can be arranged in one row. The wells in the microfluidic chip can be arranged in a staggered pattern. The wells in the microfluidic chip can be arranged in two rows.

The microfluidic device can include an integrated deformation damping well. The deformation damping well can be a thin rectangular well.

The microfluidic device can further include a first portion defining the wells and microchannel grooves and a second portion adjacent to the first portion and sealing the microchannel grooves. Either or both of the first portion and the second portion can be fabricated from soft materials. The microfluidic device can be supported by an additional layer of hard material. The hard material can be thermoset plastic. The hard material can be glass. The soft material can be silicone rubber.

The microfluidic device can include: a first portion defining microchannels and a second portion defining wells and supply channels, which are interfaced with the microchannels of the first portion. The first portion and the second portion can be bonded with an adhesive. The first portion and the second portion can be thermally bonded together. The first portion can be fabricated from hard materials. The first portion can be fabricated from soft materials. The second portion can be fabricated from hard materials. The second portion can be fabricated from soft materials. The hard material can be thermoset plastic. The hard material can be photoresist. The hard material can be glass. The soft material can be silicone rubber.

The interface can be adapted and configured to provide pneumatic connectivity to supply pressure to the one or more wells. The holding interface can be adapted and configured to provide electrical connectivity to the one or more wells.

The microfluidic device can be held between at least two components, which are tightened around the device by mean of a screw. The microfluidic device can be held between at least two components, which are tightened by an eccentric shaft. The microfluidic device can be adapted and configured to be held against the interface by one or more hooks. The microfluidic device can be held to the interface by an adhesion layer. The microfluidic device can be held to the interface by magnets. One or more magnetically susceptible components can be incorporated into the microfluidic device. The microfluidic device can be held to the interface by vacuum.

The microfluidic device can be held between at least two portions. The at least two portions can be connected to each other by hinges. The at least two portions can be connected to each other by hooks. The at least two portions can be connected to each other by a screw. The at least two portions can be connected to each other by magnets.

The microfluidic device can be held by grips that extend into the wells and seal the wells. The wells can be in communication with a common pressure source. Each well can be in individual communication with a pressure source.

A pressure-tight seal can be formed around the well between the microfluidic device and the holding interface. The seal can be formed when the interface is pressed against a soft surface of the microfluidic device by means of a flange on the interface. The seal can be formed when the interface is pressed against a soft surface of the microfluidic device by means of a flange on the device. The seal can be formed when the interface is pressed against a hard surface of the microfluidic device by means of a flange on the microfluidic device and a gasket. The seal can be formed when the interface is pressed against a hard surface of the microfluidic device by means of a flange on a gasket. The seal can be formed when the interface is pressed against a hard surface of the microfluidic device by means of a flange on a gasket, which extends into the well for sealing. The seal can be formed when the interface is pressed against a hard surface of the microfluidic device by means of a flange, which extends into the well for sealing. The seal can be formed when the interface is pressed against the microfluidic device by means of an intermittent adhesion layer.

The interface can include one or more interchangeable ports.

The interface can be coupled to the positioning device via an attachment arm. The attachment arm can be a cylindrical rod. The cylindrical rod can be between about 5 mm and about 10 mm in diameter. The cylindrical rod can be between about 6 mm and about 8 mm in diameter. The cylindrical rod can be between about 10 cm and about 20 cm in length. The attachment arm can be a non-cylindrical bar.

The interface can include one or more tubes adapted and configured to facilitate pneumatic connectivity with the one or more wells, through which the pressure in the wells can be controlled. The tubes can be positioned on a side of the interface. The tubes can be positioned on a top of the interface. The tubes can be positioned on a back side of the interface. The tubes can be positioned within the attachment arm of the interface. The tubes can have an inner diameter between about 0.5 mm and about 1 mm. The tubes can have an inner diameter between about 1 mm and about 2 mm.

The interface can include one or more electrode adapted and configuration for interfacing with a liquid in the one or more wells.

The microfluidic device can include one or more channel-embedded electrodes. The channel-embedded electrodes can be fabricated from metal. The channel-embedded electrodes can be fabricated from a conductive polymer composite.

Another aspect of the invention provides a method for utilizing a microfluidic device. The method includes: providing a device as described herein; positioning the device adjacent to a microscope; and actuating the interface to operate the microfluidic device.

This aspect of the invention can have a variety of embodiments. The microscope can be an upright microscope. The microscope can be an inverted microscope.

The microfluidic device can be held at a defined angle relative to a surface of a sample receptacle. The defined angle can be between about 10° and about 70°.

The method can further include utilizing a laboratory micromanipulator to position the device. The microfluidic device can be operated to deliver solution to the open volume in order to superfuse an object of interest. The microfluidic device can be operated to extract solution from the open volume in order to collect a release from an object of interest.

The microfluidic device can be a microfluidic pipette. The microfluidic device can be a flow-recirculating microfluidic device.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "about" is understood as within a range of normal tolerance in the art, for example within 2 standard deviations of the mean. "About" can be understood to encompass deviations within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the terms "comprises," "comprising," "containing," "having," and the like can have the meaning ascribed to them under U.S. patent law and can mean "includes," "including," and the like.

The term "freestanding" indicates that a device is independently supported. For example, embodiments of the microfluidic devices described herein are held in a freestanding manner by an interface so that the microfluidic device is supported independently of another laboratory apparatus such as a microscope.

By "microfabrication" is meant to refer to a set of techniques used for fabrication of micro- or nanostructures. In certain embodiments, microfabrication includes, but is not limited only to, the following techniques: photolithography, electron beam lithography, laser ablation, direct optical writing, thin film deposition (spin-coating, spray coating, chemical vapor deposition, physical vapor deposition, sputtering), thin film removal (development, dry etching, wet etching), replica molding (soft lithography), embossing, forming or bonding.

By "microchannel" is meant to refer to a tube with nano- or microscopic cross-section. In certain embodiments, a microchannel or channel has a size in the range of 0.1-200 μm. In other embodiments, of the present invention, microchannels are fabricated into microfluidic devices by means of microfabrication.

By "macrochannel" is meant to refer to a tube of size larger than a microchannel (>200 μm)

By "channel" is meant to refer to either a microchannel or a macrochannel.

By "channel-embedded electrode" is meant to refer to an electrically conducting solid inside a channel.

By "microfluidic device" is meant to refer to the microfabricated device comprising microchannels or circuits of microchannels, which are used to handle and move fluids. Preferably, microfluidic devices can include components like junctions, reservoirs, valves, pumps, mixers, filters, chromatographic columns, electrodes, waveguides, sensors etc. Microfluidic devices can be made of polymer (e.g., PDMS, PMMA, PTFE, PE, epoxy resins, thermosetting polymers), amorphous (e.g., glass), crystalline (e.g., silicon, silicon dioxide) or metallic (e.g., Al, Cu, Au, Ag, alloys) materials. In certain embodiments, a microfluidic device can contain composite materials or can be a composite material. The microfluidic pipette is a microfluidic device.

By "object of interest" is meant to refer to the material entity to be stimulated, studied, investigated or otherwise influenced by means of the microfluidic device.

By "open volume" is meant to refer to the liquid reservoir that encapsulates the objects of interest.

By "open volume container" is meant to refer to physical boundaries of the liquid open volume. Preferably, these boundaries comprise three dimensional boundaries such as full or partial enclosures, two-dimensional boundaries such as surfaces or capillary outlets.

By "channel exit" is meant to refer to an open end of a channel that leads into the open volume.

By "well" is meant to refer to a part of the device, which is a solution reservoir for reagents.

By "free-standing microfluidic device" is meant to refer to microfluidic device that does not have a fixed connection to the open volume, but can be moved and positioned independently from and relative to the open volume.

By "positioning device" is meant to refer to a device, which moves an object attached to it in xyz direction (and optionally rotates it).

By "tip" or "sharp tip" is meant to refer to a sharp ended protrusion out of or from the device body. In certain embodiments, a tip size is in the size range of 1-1000 μm.

By "microfluidic pipette" is meant to refer to a free-standing microfluidic device, which has sharp tip and a channel exit or several channel exits close to or at the sharp tip.

By "holding interface" or "holder" is meant to refer to a device, which can hold a free-standing microfluidic device and provides connectivity.

By "manifold" is meant to refer to a part of the holder, which provides pneumatic or electric connectivity between external tubing or cabling and the content of the wells of the microfluidic pipette.

By "attachment arm" is meant to refer to a part of the holder, which provides suitable distance between manifold attached microfluidic pipette and positioning device.

By "elastomeric" is meant to refer to a material's ability to resume its original shape when a deforming force is removed. Elastomeric materials are also refers to as elastomers. Examples of suitable elastomers include acrylonitrile-butadiene rubber, hydrogenated acrylonitrile-butadiene rubber, fluorocarbon rubber, perfluoroelastomer, ethylene propylene diene rubber, silicone rubber, fluorosilicone rubber, chloroprene rubber, neoprene rubber, polyester urethane, polyether urethane, natural rubber, polyacrylate rubber, ethylene acrylic, styrene-butadiene rubber, ethylene oxide epichlorodrine rubber, chlorosulfonated polyethylene, butadiene rubber, isoprene rubber, butyl rubber, and the like.

By "soft material" is meant to refer to a material, which is easy to deform, for example, with an elastic modulus less than 1 GPa. Examples of suitable materials are elastomeric materials, such as polydimethylsiloxane, and soft polymer materials such a polyethylene.

By "hard material" is meant to refer to material, with high elastic modulus, for example, an elastic modulus greater than 1 GPa. Examples are ceramics, metals, oxides, silicon hard plastics, such as epoxies, polycarbonates, and the like.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 can comprise 1 to 10, 1 to 20, 1 to 30, and 1 to 40 in one direction, or 50 to 40, 50 to 30, 50 to 20, and 50 to 10 in the other direction.

DESCRIPTION OF THE DRAWINGS

FIGS. 1A-1G depict a layout of a free-standing microfluidic device 0101 with sharp tip 0102 and integrated wells 0103 for reagents or solutions. FIG. 1A is a schematic top view. FIG. 1B is a schematic side view. FIG. 1C is a schematic top view of the sharp tip, where channels 0104 exit the sharp tip of the device. FIG. 1D is a schematic side view of the sharp tip, where channels are sealed with a thin membrane 0105. FIG. 1E is a schematic front view of the sharp tip. FIG. 1F is a projection view of same device. FIG. 1G is a photograph of an exemplary device.

FIGS. 2A-2D provide an exemplary illustration of geometries of the wells (0202-0204), which can be circular or rectangular or rectangular with rounded corners, as shown in FIGS. 2A-2C, respectively. FIG. 2D is an exemplary illustration of usage of smaller (0205) and larger (0206) wells in the same device 0201.

FIGS. 3A-3B show an exemplary connectivity of wells 0301 with microchannels 0302. The microchannel can directly interface with the well as shown in FIG. 3A or can be connected through orifice 0303, which is smaller than the bottom of the well, as depicted in FIG. 3B.

FIGS. 4A-4C show exemplary layouts of wells 0402 in single, staggered and double rows, which are corresponding to FIGS. 4A-C respectively.

FIG. 8 shows an exemplary assembly of a composite microfluidic device, which is made from tip section 0804 containing microfluidic circuitry, and macroscopic body 0801, which contains wells 0802 and macroscopic interface channels 0803 from the wells to the tip.

FIGS. 9A and 9B show the device in inverted and up-right microscopy setups, respectively.

FIGS. 10A-10B show photographs of exemplary setups of microfluidic device 1001 in a typical experiment using a confocal microscope. FIG. 10A shows a front/side view; FIG. 10B shows a rear/side view of the device within the setup.

FIG. 11 shows a conceptual holding interface, where microfluidic device 1101 is mechanically attached 1103 to manifold 1102 with pneumatic connectivity 1104. Manifold is further connected to attachment arm 1105, which can be used to connect to micromanipulator.

FIGS. 12A-12H show exemplary attachment methods for attaching microfluidic device 1201 to holding interface, comprising manifold 1202 and attachment arm 1203. Tight contact between the microfluidic device and the holder can be established using screw 1205 (FIG. 12A), eccentric shaft 1206 (FIG. 12B), hooks 1208 (FIG. 12C), adhesion 1210 (FIG. 12E), hinges 1212 (FIG. 12E-F), magnets (Figure G), or vacuum 1216 (FIG. 12H).

FIG. 13A shows components separately, while FIG. 13B shows the final assembly of device and holding interface.

FIG. 17B shows a side view of the front of the composite microfluidic device showing the SU-8 tip 1704 and elastomeric macroscopic body 1705, which contains solution storage wells 1706 and a deformation damping well 1707. FIG. 17C shows the composite microfluidic device mounted in a holding interface.

FIG. 18C further shows an exemplary electrical interface for devices containing channel-embedded electrodes.

FIG. 22A shows schematics of directed re-circulated flows. FIG. 22B shows the concentration profile of the re-circulation zone, showing fluorescein concentration vs. position from the channel outlet. FIGS. 22C-22E show fluorescence micrographs (fluorescein) of the microfluidic pipette in re-circulation operation showing 50 µm channels at different re-circulation pressures; C: 102 mBar/−279 mBar. D: 235 mbar/−279 mBar E: 81 mBar/−74 mBar.

DETAILED DESCRIPTION

Figures 5A, 5B, 5C:
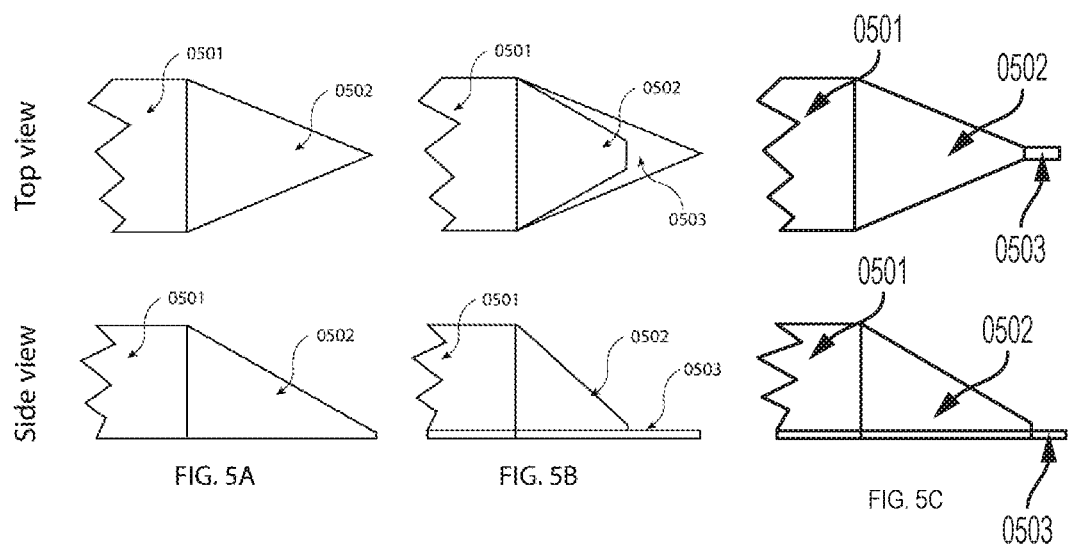
FIGS. 5A-5C show exemplary geometries of tip 0502 of microfluidic device 0501.

To solve various practical difficulties with existing microfluidic devices, such as optical non-transparency and inaccessibility of the sample, Applicant previously disclosed a free-standing microfluidic pipette in International Application No. PCT/US10/58926, which allows contamination free control of the solution environment around microsized samples, easy positioning, fast solution switching capability, unproblematic brightfield imaging and facile combination with other free-standing probes.

This disclosure further describes preferred device configurations, interfacing and holding schemes, to improve usability of this free-standing microfluidic device and to reduce setup time, with the application focus on microscopy experiments. The present device satisfies previously unaddressed needs in the context of free-standing microfluidic devices. We have embedded solution wells into the free-standing device, which saves chemicals due to extremely small dead volumes, compared to external tubing. For disposable devices, the contamination risk and the need for cleaning the interface tubes are eliminated. Furthermore, embodiments of the invention provide narrow elongated device designs with a sharp tip, which is optimal when applied in spatially-confined microscopy setups, for example with confocal microscopes. It reduces collisions with other setup components such as the microscope stage, the condenser lens, the microscope objective, or cell culture dishes, and reduces shadows cast by the device in the brightfield image.

As will be readily appreciated by one of ordinary skill in the art, the aspects and embodiments of the invention described herein are compatible with the disclosures of International Application No. PCT/US10/58926. For example, the microfluidic devices described herein can be utilized to generate a circulation zone in a desired region (e.g., around a specific cell).

The embodiments of this invention provides means to suitably interface free-standing microfluidic devices with microscopy experiments in the field of physics, chemistry, biology and medicine, where microscale objects need to be locally exposed to chemicals.

The present invention features a free-standing microfluidic device 0101 (as referred to also a "microfluidic device" or "device"), which features wells for solutions 0103. Incorporating wells into the device 0101 reduces dead volumes, otherwise created by tubing, also reduces the amount of reagents needed in experiments. In some preferred settings, the device itself is a disposable part. As all chemical or biological solution needed for operation are supplied from the integrated wells of the device, absorption of chemicals to the channel walls and contamination risk of the supply tubes are reduced. In one configuration, solutions in the wells do not come in to contact with the non-disposable parts of the setup, reducing the need for cleaning. In some preferred settings, channels 0104 of the microfluidic device are in the ranges of 10-20 μm or in the ranges of 20-50 μm, or in the ranges of 50-100 μm with preferable operation pressure in the vacuum range of −100 kPa to 0 kPa, and for overpressure in the range between 0 kPa to 100 kPa, which can give preferable flow rates in the range between 1-500 nL/s. To optimize solution consumption during device operation, the flow rates can be adjusted. To supply or collect solutions, the wells can be in preferable size ranges from 10 to 50 μL or from 50 to 100 μL or from 100 to 500 μL. By shape, wells can be, in some embodiments, either circular 0202 or rectangular 0203 or rectangular with rounded corners 0204. Circular wells feature good structural strength and easier release from molding during manufacturing. On the other hand rectangular channels can be packed more densely for more optimal usage of space. In one embodiment, the wells are equal in size and geometry (FIGS. 1A-1G), which facilitates the usage of one or more universal holders for device with different internal circuitry. In another embodiment, the wells are of different size to accommodate the need of larger solution volumes in some experiments (FIG. 2D). In a third embodiment, wells of equal size can be connected in parallel in order to accumulate volumes and increase operation time after loading the devices.

In one exemplary embodiment, channels 0302 can be connected to well 0301 directly at the well bottom. In another exemplary embodiment, channels 0302 can be connected to well 0301 through orifice 0303. In this case, the diameter of the orifice is smaller than the bottom of the wells. It can be preferable to optimize space usage, such that other channels 0304 can be placed underneath the well 0301.

Wells 0402 can be arranged in different patterns (FIGS. 4A-4C). In one embodiment, the wells are arranged in a single row (FIG. 4A). This arrangement keeps the device narrow, which is favorable to apply it in space-confined microscopy environments. It also facilitates usability by, for example, enabling easier loading. In another embodiment, the wells can be arranged in a staggered (FIG. 4B) or double row pattern (FIG. 4C), which increases the number of wells and thus the number of possible different solutions and controls. Compared to a single row arrangement, it also reduces the length of the device, which can be favorable due to manufacturing reasons, where handling very long and narrow device might be more difficult. It also reduces differences in length of different channels, which connect the device tip with different wells, facilitating the necessary balancing of hydrodynamic resistances. It can be less favorable from the point of view of handling the device, since a broader device could interfere with other parts of the setup. In some embodiments, the wells can be spaced according to microtiter plate standards, for example 4.5 mm and 9 mm.

To bring the channel openings as close as possible to the objects of interest with minimal disturbance of the surrounding environment, the device 0501 has sharp tip 0502. This sharp tip 0502 can have, in one embodiment, pyramidal geometry as depicted in FIG. 5A. In another embodiment depicted in FIG. 5B, the tip has a flat geometry 0503, which is cut to a sharp rectangular shape. In a third exemplary embodiment depicted in FIG. 5C, the tip has a rectangular flat shape.

These microfluidic devices can be made of soft or hard materials or of a combination of both. Examples of soft materials include silicone elastomers (e.g., polydimethyl siloxanes rubbers). Examples of hard materials include hard thermoplastic materials, such as polycarbonates, polyethyleterephtalates, polyacrylates or mineral materials such as glass. Soft materials are favorable due to easier fabrication, and non-fragile properties. In another preferable embodiment, a soft material device can be partly bonded to a hard material substrate for structural support. Hard materials are favorable due to non-deformability and possibility to make long and sharp tips, which maintain structural strength.

Figure 6:
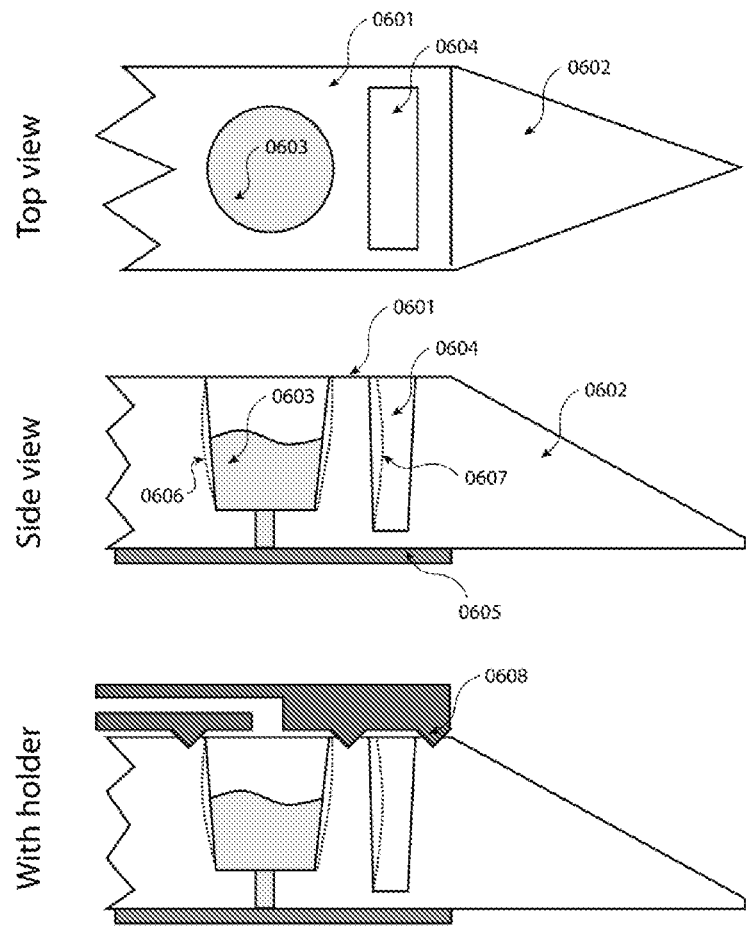
FIG. 6 shows deformation damping well 0604, which is used to reduce and prevent motion of the tip 0602, in case of elastomeric device body 0601.
Figure 7:
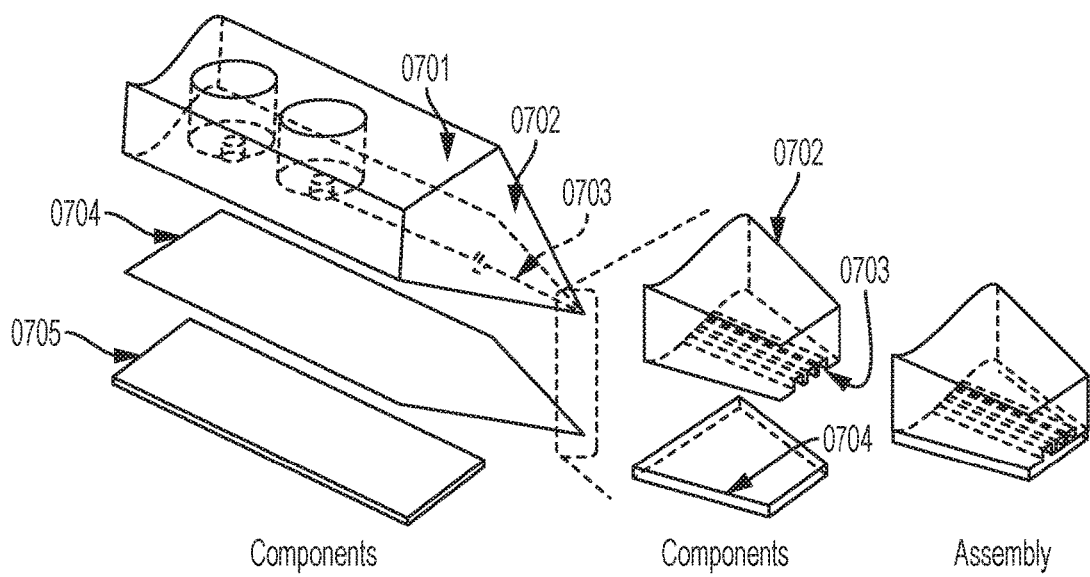
FIG. 7 shows another exemplary assembly of the microfluidic device, where microchannel grooves 0703 are molded directly into device body 0701 and sealed with thin film 0704.
Figure 9A:
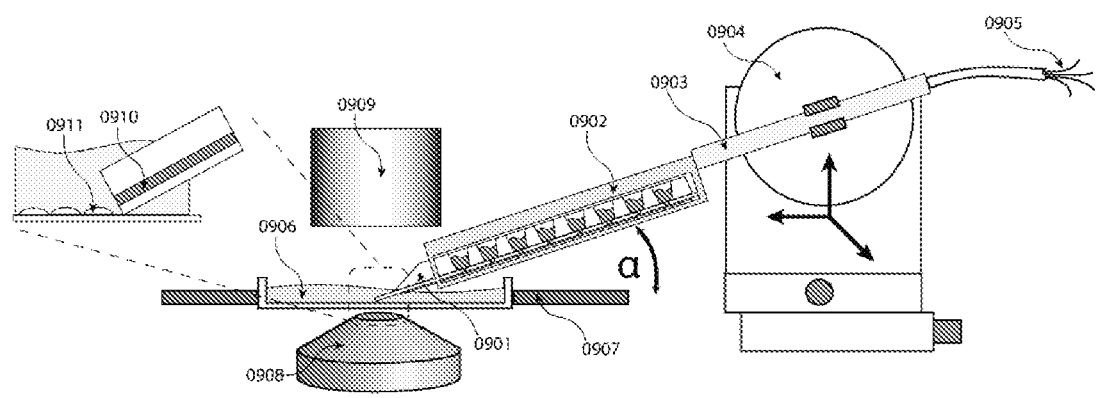
FIGS. 9A-9B depict a freestanding microfluidic device in an exemplary experimental setup. Microfluidic device 0901 is held by holding interface 0902, which can be positioned with micromanipulators 0904 under microscope 0908/0909.
Figure 9B:
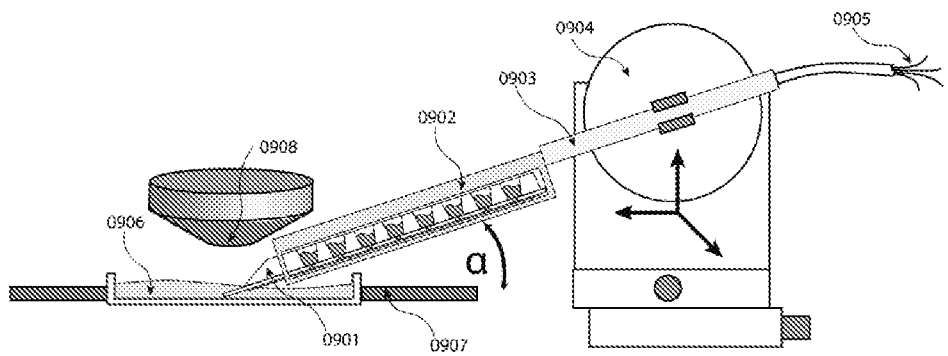

In some embodiments, elastomeric device 0601 can contain a deformation damping well 0604, which reduces motion of the tip caused by deformation of the one or more wells due to changes in the pressure of the solution in the wells. In this case (depicted in the bottom two views of FIG. 6), one wall of the deformation damping well 0604 is deflected 0607, but this deflection is absorbed and not transferred over the absorption well 0604, thereby reducing motion of the tip. In one embodiment, the elastomeric device has support 0605 underneath the device, such that the support 0605 covers the bottom area of the deformation damping well. In another embodiment, the holder grips the device firmly on either side of the deformation damping well 0608.

In one preferable embodiment, the channel grooves and wells can be fabricated into one monolithic part 0701. In order to form closed channels, a thin material layer 0704 can be bonded to the device, sealing the channel grooves 0703 and form closed channels. In some embodiments, the thin material layer has a thickness in the range of 1-100 μm. In further embodiments, the thickness of the thin layer is 5-25 μm. In other embodiments, the thickness of the thin layer is 0.2 to 10 times the channel width. In some preferable embodiments, the thin material layer can be further supported by a thicker layer of another material 0705, which can cover some parts of the device, leaving the sharp tip 0702 exposed. In one embodiment, these materials can be elastomeric. In another embodiment, the supporting layer material can be hard plastics or glass. One preferred exemplary material combination is polydimethylsiloxane (PDMS) for the device and the thin material layer, and glass for the supporting layer. In one preferred method, the device can be made by PDMS molding, the thin material layer by PDMS spin-coating, and the supporting layer can be fabricated from glass. The individual layers can be bonded using plasma bonding or wet bonding. The sharp tip can be defined by mechanical cutting.

In another preferable embodiment, the microfluidic device comprises of two parts (FIG. 8). The first part is a microfluidic device 0804, the second part is a fluidic device 0801, which contains wells 0802 and channels 0803, connecting the wells to the inlets of the first part. In one preferable embodiment, the two parts can be bonded by a layer of adhesive 0805. This two-part design is preferable to reduce the costs of the microfluidic part. Non-limiting examples could be microfabrication of the small tip with microchannels 0806 into photoresist, glass or silicon, which are more expensive materials suitable for high precision fabrication. The wells can in some embodiments require much more space and could be fabricated separately using cheaper, more commonly used plastics, such as polystyrene, polyethylene, or polypropylene. Electrodes or other structures can be easily integrated during fabrication.

Furthermore, this invention provides a holding interface 0902 for the free-standing microfluidic device 0901. The purpose of the holder is to mechanically hold and support the microfluidic device, and to control its position and angle towards the object of interest. The holder also interfaces the external pressure source to the wells of the microfluidic device through tubing 0905. In an embodiment, the holder has an elongated shape 0902 with extended rod 0903, which can be connected to manipulator 0904, located close to the microscope 0908. The manipulator is typically 10-30 cm away from the objective, which is one exemplary preferred length of the rod. The elongated shape of the holder is favorable due to the typically confined space in many microscopy setups. In an embodiment, the holder has only very few components beneath the bottom of the microfluidic device to minimize the risk of collision with microscope stage 0907 or the edges of open volume reservoirs 0906, for example cell culture dishes. Holder components under the device can also increase the minimum application angle (a). Small application angles are favorable, to avoid shadow formation caused by the tip of the microfluidic device and the holder, affecting the imaging light path. The full range of application angles can be from 0° to 90°. In many practical situations preferred range is in the range of 0° to 5°, 5° to 10°, 0° to 45°, and the like.

In another embodiment, the holder has only a few components above the microfluidic device near its tip. This avoids collision with optical components of the microscope such as condenser 0909, in case of an inverted microscope, or objective 0908, in case of an up-right microscope, as well as reducing possible shadowing. In some embodiments, the holder can optionally have one or more electrical connectors 1107 to either the microfluidic device (if it has integrated electrodes) or to the liquid inside the wells.

Figure 12A:
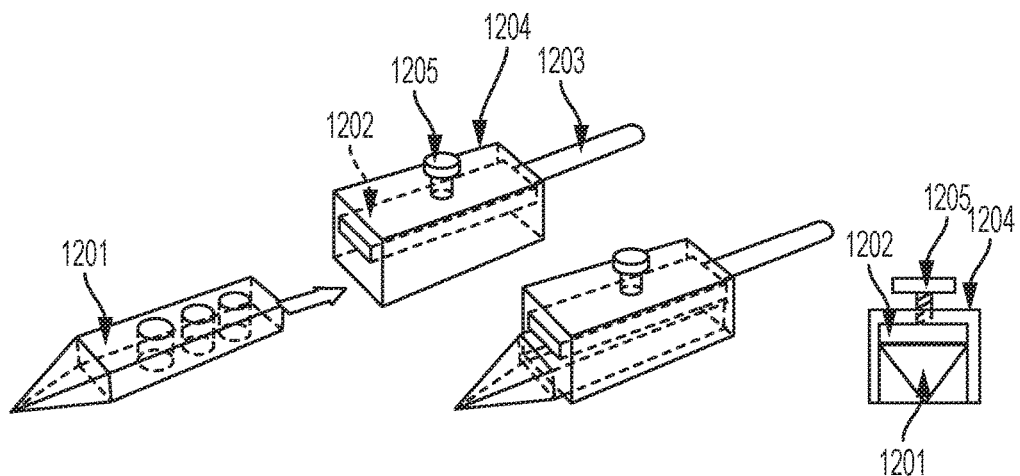
Figure 12B:
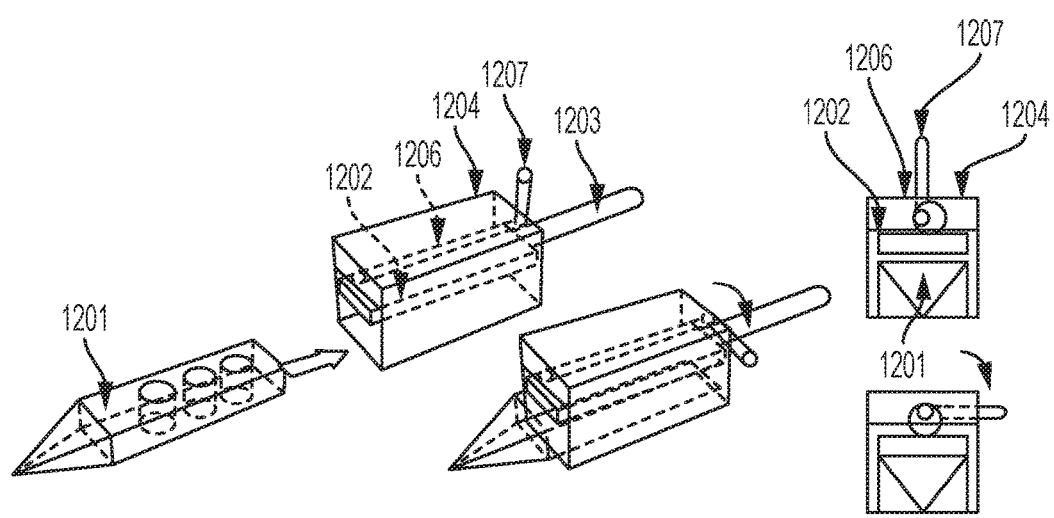
Figure 12C:
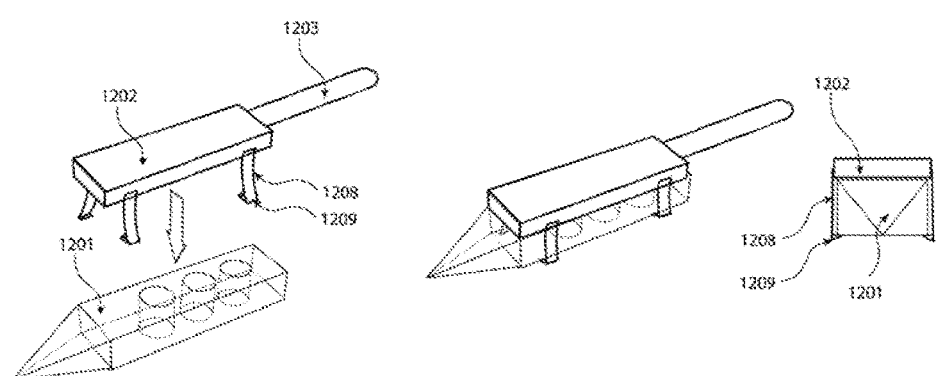

Attaching the microfluidic device to the holder can be done in various ways (FIGS. 12A-12H). In one exemplary embodiment, device 1201 is attached by squeezing it between two parts of the holder, where one part is a cage 1204 around the device. The other part is a manifold 1202 with pressure connection interface, which is pressed against the device from the top. The two parts can be tightened either by screw 1205 (FIG. 12A) or by an eccentric shaft 1206 (FIG. 12B), which determines the distance between cage and manifold. This shaft can be turned with lever 1207. In another embodiment, the device is held by hooks 1209, which are further attached to flat bendable strips (FIG. 12C). The hooks 1209 secure the microfluidic device by pressing it against the holder. For a tight seal, such a construction can include a soft material layer or gasket in between the top layer of the microfluidic device and the holder. In one embodiment, the entire device can be elastomeric, while supported from the bottom with a hard layer. In one embodiment, the device can be fabricated from PDMS and the supporting layer from glass.

Figure 12D:
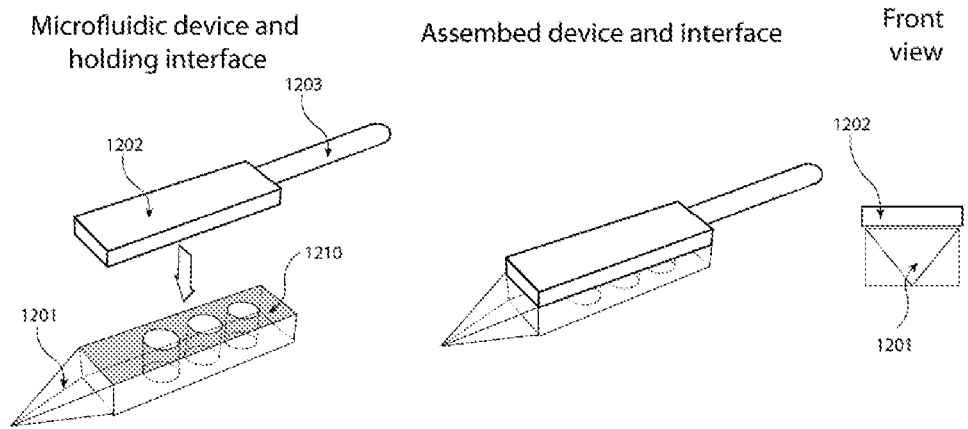
Figure 12E:
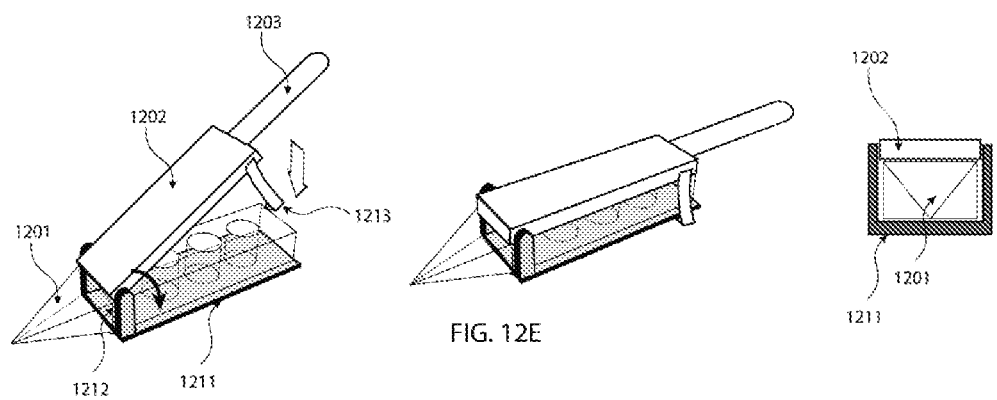
Figure 12F:
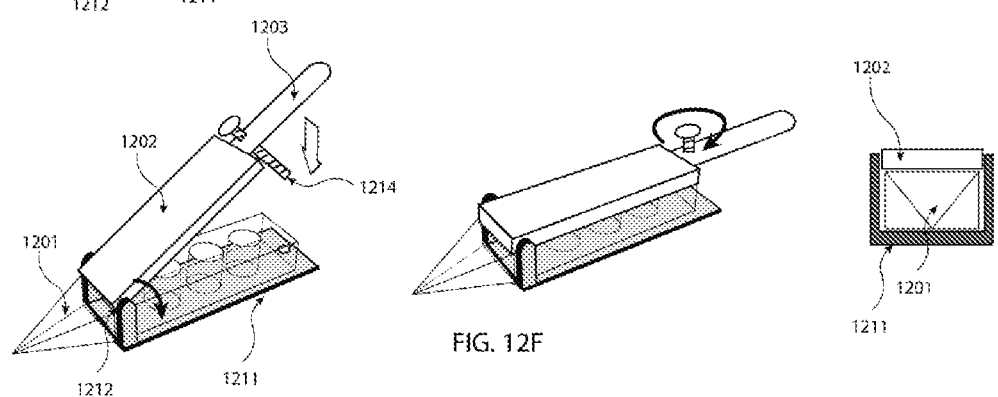

In yet another embodiment, the device can be held by an adhesion layer 1210, which reversibly interconnects microfluidic device and holder (FIG. 12D). The adhesion can be achieved by means of a chemical adhesive or interaction between a magnetic component and a magnetically susceptible material, incorporated into the device. Such embodiment is favorable to avoid holder parts underneath the microfluidic device. In another embodiment, the microfluidic device can be clamped between two holder parts (1202 and 1211), which are connected with each other by means of hinges 1212 (FIG. 12E-G). In the clamped state, the two parts can be fixed around the microfluidic device by means of hooks 1213 (FIG. 12E), screws 1214 (FIG. 12F), or magnets (FIG. 12G). In yet another embodiment, the device can be held by vacuum applied to a groove 1216 in manifold 1202 (FIG. 12H). In an embodiment, the holder is constructed such that it is self-aligning around the microfluidic device, ensuring that the pneumatic connections in the holder and the wells in the device are aligned with each other. In one embodiment, this is achieved by an enclosure, which fully or partly surrounds the device, for example the bottom plane of the device, or the top plane of the device, such that the device is directed to a predefined position on or inside the holder, before the device is clamped into the holder and tightened. In some embodiments, an auxiliary component is used to assist this process such that the device and the holder are aligned before they are attached to each other. This is particularly suited for the holders shown in FIGS. 12C-D.

Figure 14A:
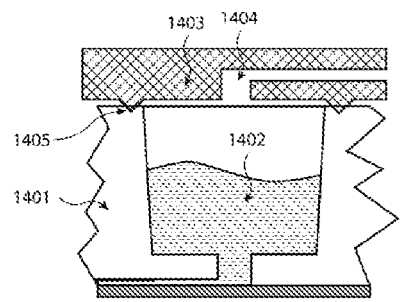
FIGS. 14A-14J show an exemplary list of methods for pressure connectivity between the well 1402 of the microfluidic device 1401 and holding interface 1403, with flanges 1405, 1406 and 1414, gaskets 1407-1410, and adhesive 1411. The connectivity allows implementation of electrodes 1412. Further holding interface can contain interchangeable port options for configurable connectivity (FIG. 14J).
Figure 14B:
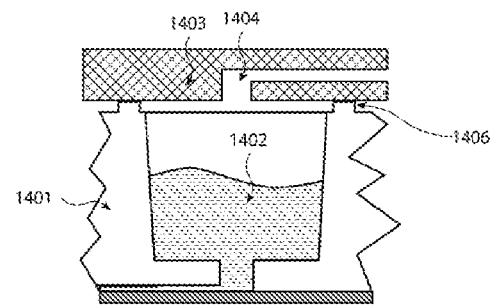
Figure 14C:
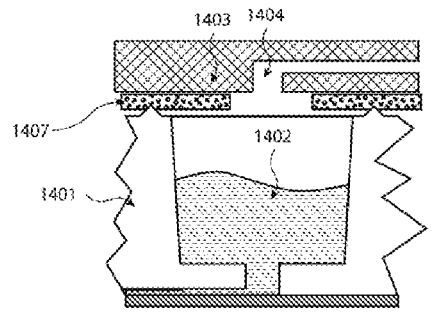
Figure 14D:
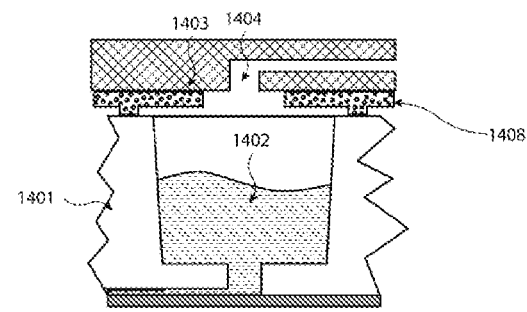
Figure 14E:
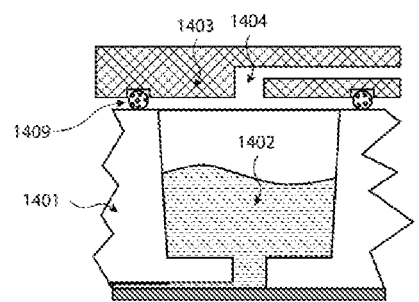
Figure 14F:
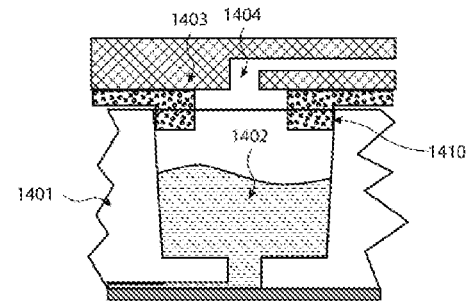
Figure 14G:
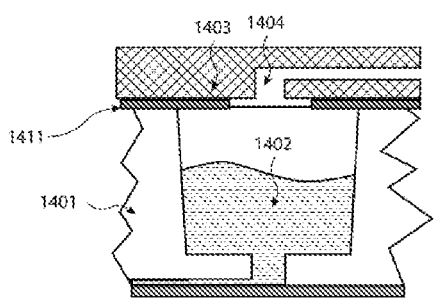
Figure 14H:
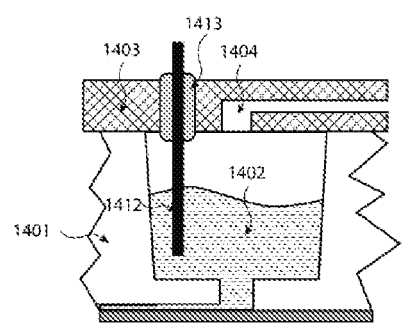
Figure 14I:
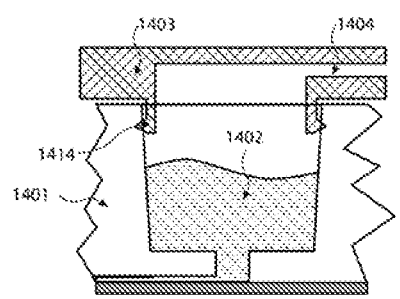

The holder can further provide a seal between the wells in the device and the pneumatic tubing to the external pressure source. In one embodiment, all wells or groups of wells can be connected to a single tube. In another embodiment, each well has its own separate tube to control pressure inside. To form a pressure tight connection between the holder and a well, several sealing methods can be used (FIGS. 14A-14J). In one embodiment, the holder 1403 has a sharp flange 1405, which in some embodiments is between 0.5 and 1.0 mm in height (FIG. 14A). This flange can be directly pushed against the elastomeric device 1401 to form a pressure-tight seal. Alternatively flange 1414 can extend into the well of elastomeric device, pushing against the walls of the well (FIG. 14I). In another embodiment, the elastomeric device has flanges 1406 that can be pushed against the hard material holder (FIG. 14B). In a third exemplary embodiment, a device made from hard material with sharp flanges is pushed against the holder with an elastomeric seal 1407 (FIG. 14C). In a fourth exemplary embodiment the connection between device and holder is sealed with a flat or embossed elastomeric seal 1408 (FIG. 14D). In another embodiment, the seal is a gasket or O-ring 1409, held in place by a groove in the holder surface, as shown in FIG. 14E. In another exemplary embodiment an embossed seal is pushed into the well (FIG. 14F). In another embodiment, protrusions from the manifold extend into the device, enabling a seal to be made to the manifold. One non-limiting example is an attachment into the well (FIG. 14I) using a flange 1414 to exert pressure into the device. In another exemplary embodiment, the device and holder are sealed using an adhesion film 1411. Such a holding interface is compatible with both soft (elastomeric) and hard material devices.

In an embodiment, the holder can contain one or more electrical wires or electrodes 1412, which connect to the contents of the well when the device is assembled. In the case of the holder being made from metal, the electrode can be isolated from the holder by an insulator 1413. Integrated electrical wires or electrodes can be favorable for electrophoretic or electroosmotic transport, electroporation, electrochemical detection, etc. In one embodiment, the integrated electrical wire connects to a channel-embedded electrode.

Figure 14J:
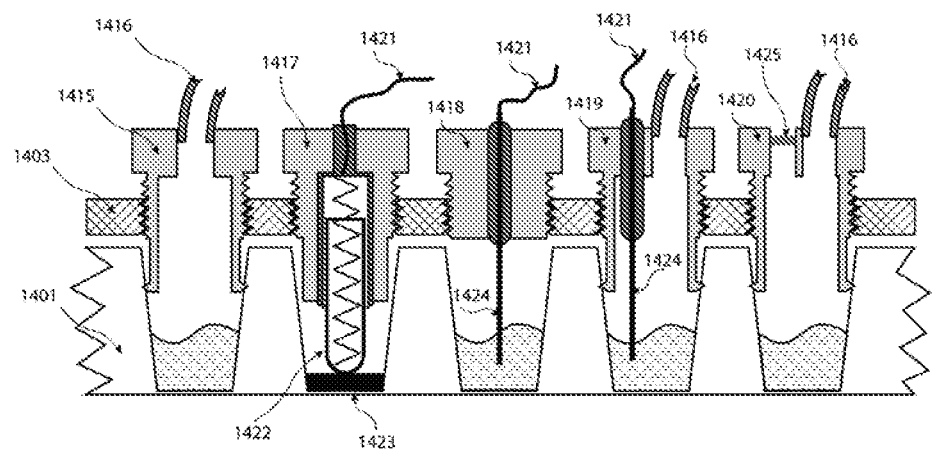
Figure 15A:
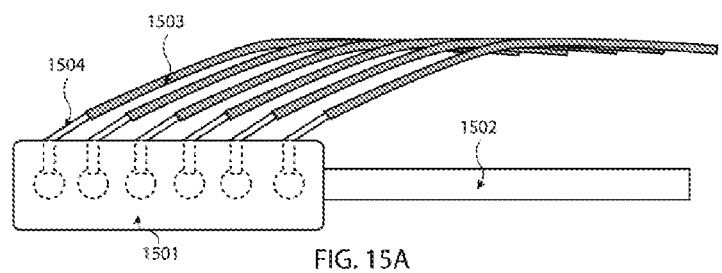
FIGS. 15A-C show examples of external tubing 1503 connected to holding interface 1501/1502.
Figure 15B:
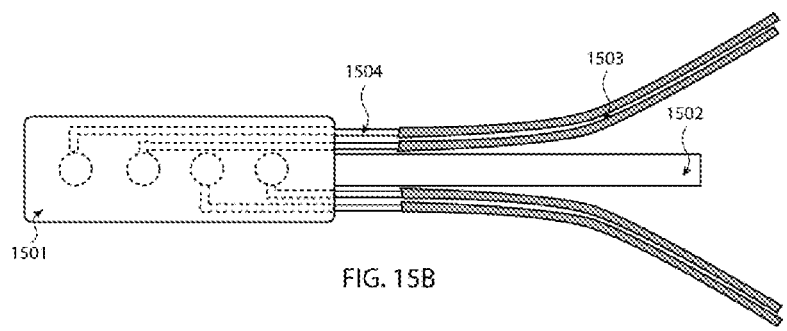
Figure 15C:
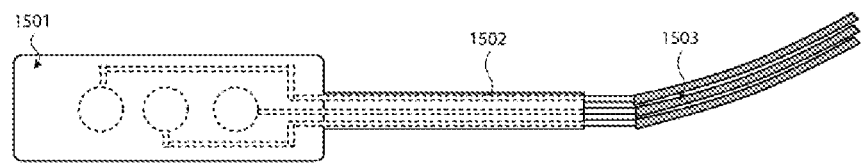
Figures 15D, 15E:
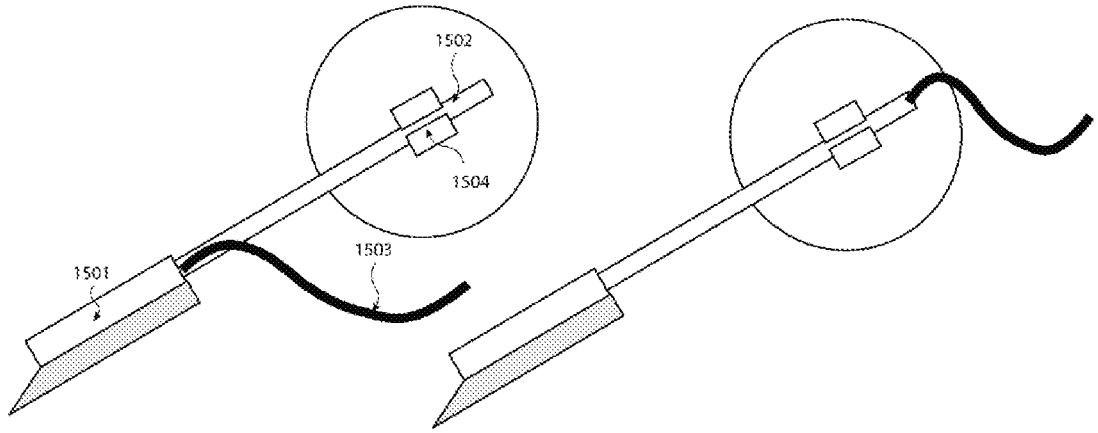
FIG. 15D-E shows tubing connection variants to the holding interface, with tubing 1503 connected either to manifold 1501 or attachment arm 1502.
Figure 16A:
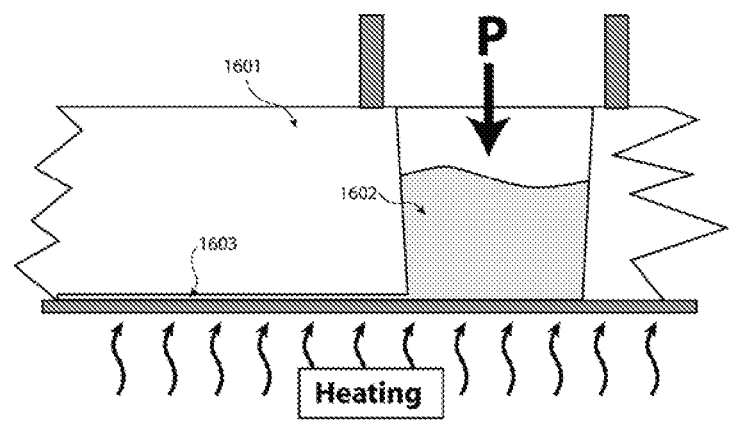
FIGS. 16A-C shows an example of a method for introducing electrodes into the device via means of filling selected microfluidic channels with a conductive medium. Preparation of the electrodes includes heating for either melting or curing of the conductive medium 1602. Exposure of the electrode material 1603 can be achieved via selected removal of channel wall material 1604.
Figures 16B, 16C:
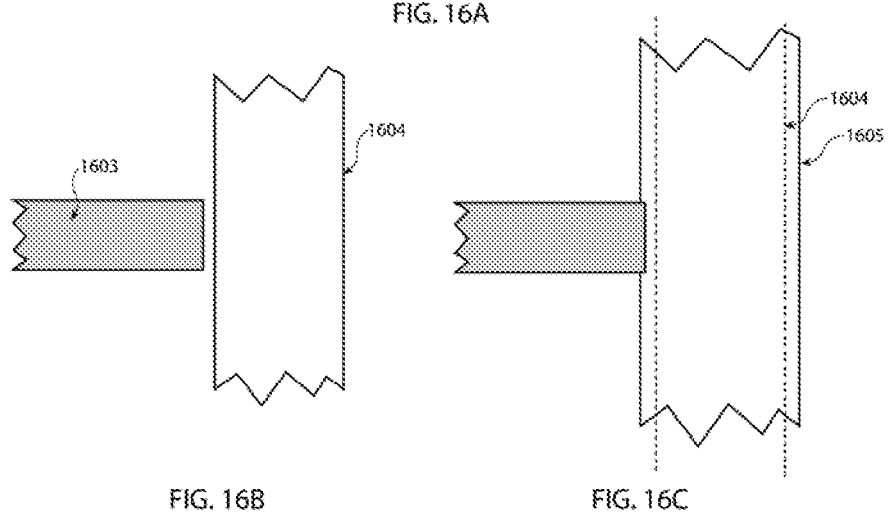

In another embodiment, the holder can contain one or more interchangeable manifold port options (1415, 1417, 1418, 1419, 1420), allowing for reconfiguration of the interfacing to the wells in the device (FIG. 14J). The manifold port can be attached to the manifold via push fitting, screw threads, adhesion, and/or clamping.

In one embodiment, an interchangeable manifold port 1415 can deliver pneumatic connectivity through a tube 1416.

In another embodiment, an interchangeable manifold port 1417 can contain a spring loaded electrical connector 1422 to form an electrical contact with the well side of a channel-embedded electrode 1423, allowing for external connection via wire 1421.

In yet another embodiment, an interchangeable manifold port 1418 can contain an electrode 1424, to form an electrical connection from the well contents to an external wire 1421.

In a further embodiment, an interchangeable manifold port 1419 can contain a combination of pneumatic 1415 and electrical 1418 connectivity.

In one more embodiment, an interchangeable manifold port 1420 can contain a septum 1425 to allow for introduction of an auxiliary component into the well, during operation of the device. This component can be a needle or capillary for addition or removal of fluid into/from the well, an electrode or an optical fiber.

Referring now to FIG. 15, the holder 1501 features ports 1504 and interfacing tubing 1503 to connect the wells to the external pressure and vacuum sources for pressure control. In one embodiment, this tubing 1503 is attached to ports at the side of the holder (FIG. 15A). This is favorable due to simple fabrication of the holder, but requires the protruding tubes to be close to the tip, which can disturb free manipulation of device and holder. In another embodiment, the tubes can be attached to ports at the rear of the holder manifold (FIG. 15B). In another embodiment, the tubes can be attached through ports in the attachment arm 1502 of the holder (FIG. 15C). This holder is more difficult to fabricate, but it keeps the tubes further away from the space-limited experimental environment. It also reduces torque acting on attachment point 1504 of positioning device 1505 and holder 1501/1502 (FIGS. 15D and 15E), which would be created if mechanical load is applied through tubing 1503. Tubes 1503 are preferably made from soft materials to minimize the load. In one aspect, the tubes 1503 should be narrow to increase flexibility and pack more tubing into the confined space around the miniature holder, and also to minimize the volume of the tubing, which needs to be filled when the external pressure is changed, thereby affecting actuation time. In another aspect, the tubes should be broad to reduce flow resistance. Too narrow tubes increase flow resistance and therefore increase solution switching times. In some preferable embodiments, the tube's inner diameter is 0.5-1 mm and the length is 1 m. In another embodiment, the tubes should be 1-2 mm in diameter.

A channel-embedded electrode can be introduced by filling a channel with metal. In one embodiment, the metal is a low melting point metal alloy. Filling of channel 1603 is achieved by heating the device 1601 to a temperature above the melting point of the metal, yet below the decomposition temperature of the device, simultaneously applying external pressure to well 1602, which is filled with molten metal alloy. In one exemplary embodiment, the metal can be Field's metal (32.5% Bi, 51% In, 16.5% Sn), Rose's metal or Wood's metal. The channel electrode can also be produced using a conductive polymer composite, flowing the non-cured material through the channels, followed by curing in place. Curing can be achieved by; light exposure, heat, or gas exposure. In some embodiments, the connection between internal liquid carrying channel 1604 and an electrode 1603 can be made by etching away the wall of the liquid carrying channel 1604 such that the channel is enlarged (1605) and the electrode is exposed into the channel. In another embodiment, the electrode is fabricated to connect the open volume with the well.

Examples

Non-limiting examples of device and holding interface fabrication are presented herein.

Materials

N-type silicon wafers, photoresist (Microchem SU8-10), and an SU8 developer were provided by the MC2 cleanroom facility at Chalmers University of Technology of Göteborg, Sweden. A Dow Corning Sylgard 184 PDMS kit was obtained from GA Lindberg of Göteborg, Sweden. Dichlorodimethylsilane was obtained from Sigma-Aldrich of St. Louis, Mo. Materials and machining of molds and holding interfaces were obtained from Hagal AB of Molndal, Sweden. PTFE tubing was obtained from VWR of Radnor, Pa.

Device Fabrication

All microfluidic molds for replica molding were prepared in the ISO100 cleanroom facility MC2 at Chalmers. PDMS molding and curing was carried out under laminar flow hood. The layout was designed in Autodesk AutoCAD 2008. Patterns for each layer were transferred to the E-beam lithography system JEOL JBX-9300FS and written to chromium coated soda-lime glass masks. Wafers were treated before use by means of oxygen plasma in the microwave plasma processor Tepla 300PC (1 mbar, 250 W for 1 min, $O_2$ gas flow 400 sccm).

The injection mold was machined, defining the 8.5 mm wide and 4.5 mm high device body 0101 with a single row of eight conical 35 µL wells 0103 separated from center-to-center by 6 mm. The length of the sharp tip was designed to be 9 mm. The fabricated device is depicted in FIG. 1G.

Photoresists were exposed on a Karl Süss MA6 contact mask aligner (G-line, 5-6 mW/cm$^2$). For the mold, SU-8 10 was spin-coated at 1600 rpm for 30 seconds, soft baked at 65° C. for 2.5 minutes, ramped to 95° C., baked at this temperature for 6 minutes (all on a hot plate) and left to cool to room temperature (RT).

Subsequently, the wafers were exposed with 5 mW/cm$^2$ UV-Light for 40 seconds through a dark field mask, post-baked 1 minute at 65° C., ramped to 95° C., baked at this temperature for 3 min and finally left to cool to room temperature. The resist was developed in SU-8 developer for 4 minutes, rinsed with developer and washed in de-ionized water (DIW). The mold was blow dried and cleaned in radio frequency (RF) oxygen plasma (50 W, 250 mTorr, 1 minute).

The mold was hard-baked at 200° C. (air circulation oven) for 30 minutes, with slow heating and cooling. The geometries of the molds were characterized with an Olympus MX40 microscope and a stylus profiler Tencor AS500 (The channel height was ~20 µm). Before use, the mold and a clean silicon wafer were anti-adhesion-treated with dichloro dimethyl silane by exposing the surfaces to the vapors under a Petri dish cover for 5 minutes. PDMS pre-polymer was prepared by mixing parts A and B in a ratio 10:1 and injection molded.

For the thin membranes, PDMS was spin-coated onto the clean wafer at 2000 rpm for 60 seconds. PDMS structures were cured at 95° C. (air circulation oven) for 1 hour. Thereafter the chip was assembled by oxygen plasma bonding in a Plasma Therm Batchtop PE/RIE at 250 mTorr, 85 W, 10 sccm $O_2$ for 10 seconds.

First, the bottom surface of the thick PDMS slab and the thin PDMS membrane, still adhered to the wafer, were treated and bonded at 95° C. (air circulation oven) for 1 hour. Then the composite was peeled off and the bottoms of the wells were punched to establish contact with the channels. The pipette tip was then shaped by means of a sharp cutting blade. The composite slab and the glass part were plasma treated and bonded. An overhang of 10 mm with respect to the glass slide edge was left. Finally, the chip was allowed to rest and complete bonding over night, reproducibly yielding a functional device.

Composite Device Fabrication

Figure 17A:
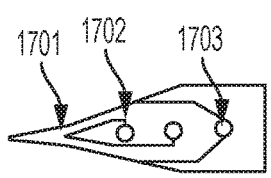
FIGS. 17A-17C show photographs of an exemplary assembly of a composite microfluidic device, which includes a tip containing microchannels, the tip made from a hard polymer (FIG. 17A), and an elastomeric macroscopic body 1705, containing solution storage wells 1706 and macroscopic interface channels.
Figure 17B:
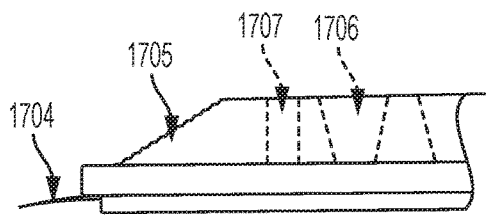
Figure 17C:
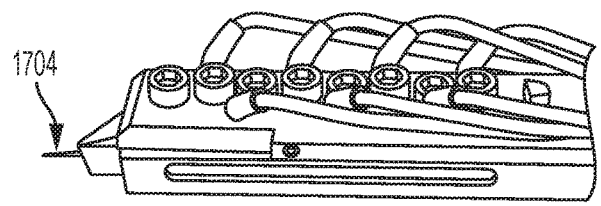

Another exemplary microfluidic device was fabricated using the composite approach depicted in FIG. 8. Exemplary photographs of the resulting device are shown in FIGS. 17A-17C. Firstly, the tip section 1704, containing microfluidic channels 1702 was fabricated from a hard polymer (photoresist SU-8) by photolithography. This tip was then interfaced with an elastomeric macroscopic body using a tape layer. The macroscopic body contains both wells and macroscopic interface channels.

Fabrication of SU-8 tip

Two Pyrex® wafers were cleaned using acetone, isopropanol and de-ionized water, blown dry and treated with microwave plasma. A thermal release tape (120 170° C.) was then applied to both the Pyrex wafers. Thereafter photoresist SU-8 10 was deposited onto the thermal release tape and spun to the desired thickness (1000 rpm for 30 seconds yielding a 30 μm film). These films were soft baked for 3 minutes at 65° C. and 10 minutes at 95° C. Directly following, the wafers were exposed to the i-line of a mercury arc lamp for 160 mJ dosing, using a mask-aligner (Karl-Süss MA6), so that one of the wafers held the structure for the device bottom layer and the other one for the device top layer. The top layer contained the liquid inlets 1703. These wafers were then both post-exposure baked for 1 minute at 65° C. and for 4 minutes at 90° C. and left to cool slowly to room temperature. The wafer holding the bottom layer then has another deposition of SU-8 10 and is spun and pre-baked according to the initial protocol, followed by relaxation at room temperature for 10 minutes. The photomask defining the microchannels was aligned to the device bottom layer, followed by exposure and post-exposure baking as described before.

Both wafers were carefully developed with SU-8 developer and cleaned with isopropanol and dry nitrogen. Thereafter the structures were aligned to each other and bonded under pressure (3 bar) at a temperature of 100° C. for 30 minutes in a substrate bonder, SUSS SB6. After bonding, the wafers were heated briefly to the release temperature of the thermal release tape, followed by slow cooling to room temperature, after which the tip sections could be removed from the thermal release tape. Finally these tip sections were hard baked at 200° C. for 30 minutes in an air circulation oven, using temperature ramping.

The macroscopic body 1705 was fabricated from an elastomeric silicon rubber (PDMS) as described for the previous exemplary device. However, in this embodiment the master for the macroscopic interface channels was machined using standard machining techniques to yield structures with approximate cross-sections of 1 mm×1 mm. The composite microfluidic device constituents, (macroscopic body, SU-8 tip and a glass support) were connected via PDMS adhesive tape obtained from Cellectricon AB of Molndal, Sweden.

Holding Interface

Figure 13A:
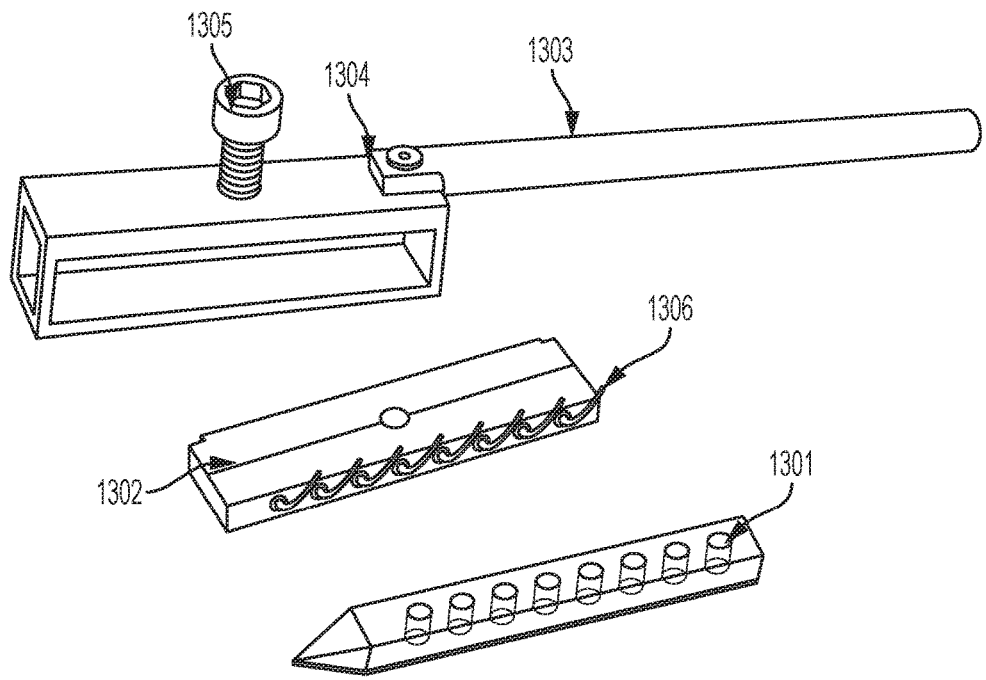
FIGS. 13A-B are photographs of both a simple exemplary microfluidic device and a holding interface.
Figure 13B:
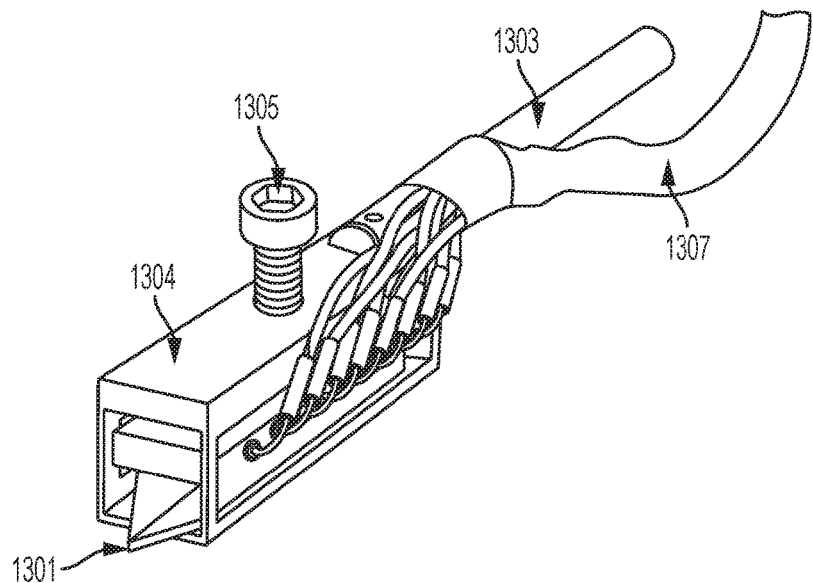

The holding interface was machined in aluminum and it contained two main parts (FIG. 13), one rectangular cage 1304 with holding rod 1303 to attach to a micromanipulator and a pressure interface manifold 1302 with sharp 1 mm thick flanges which push into the soft PDMS around wells 1301. Thin metal tubes 1306 with 0.85 mm outer diameter were fixed into the manifold and 0.8 mm inner diameter, 1 m long Teflon tubing 1307 was attached to the tubes. Cage and manifold were tightened around the microfluidic part using a screw 1305. This holding interface was tested to withstand pressures between −1 bar to +1 bar relative to atmospheric pressure.

Figure 18A:
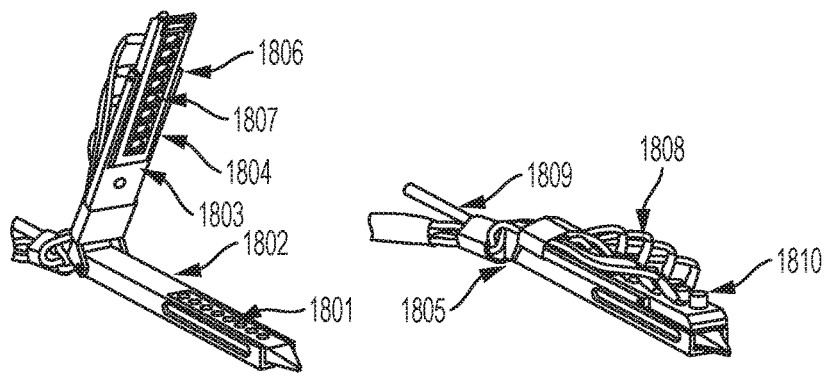
FIGS. 18A-18C show photographs of an exemplary holding interface. For clarity, the interface is shown in both an opened (FIG. 18A) and closed (FIG. 18B) configuration, containing a microfluidic device 1801.
Figure 18B:
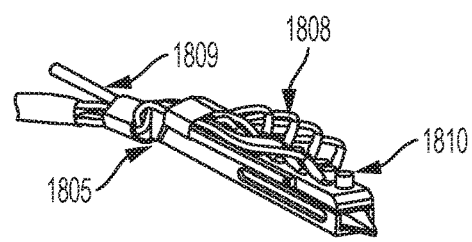
Figure 18C:
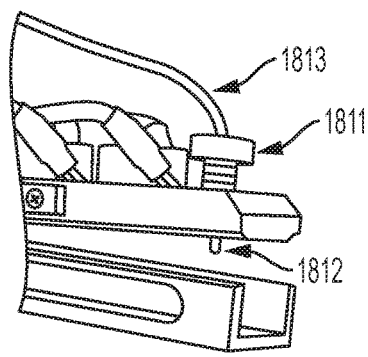
Figure 19:
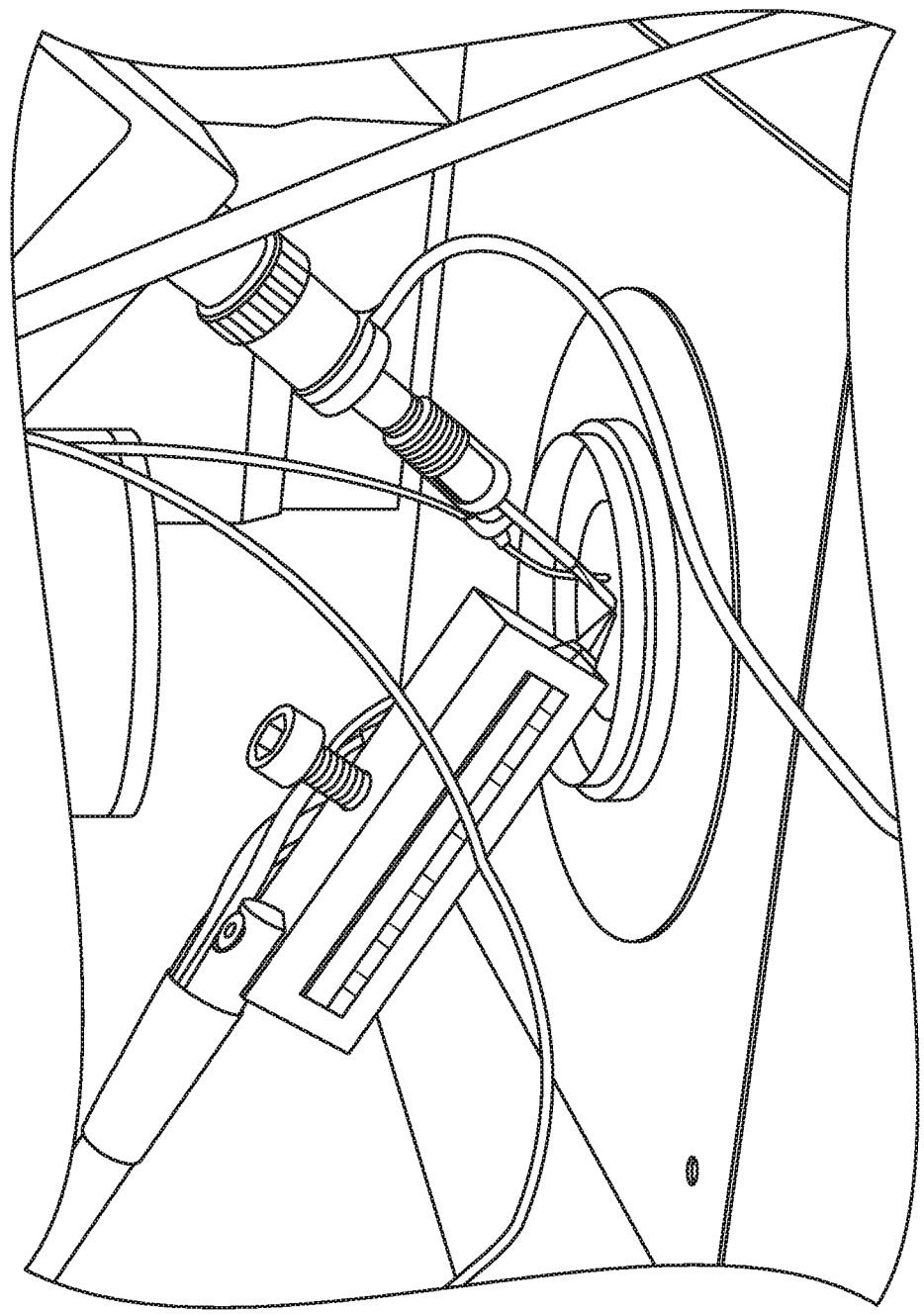
FIG. 19 is a photograph of a microfluidic pipette together with patch-clamp pipette under fluorescent microscope according to an embodiment of the invention.
Figure 20:
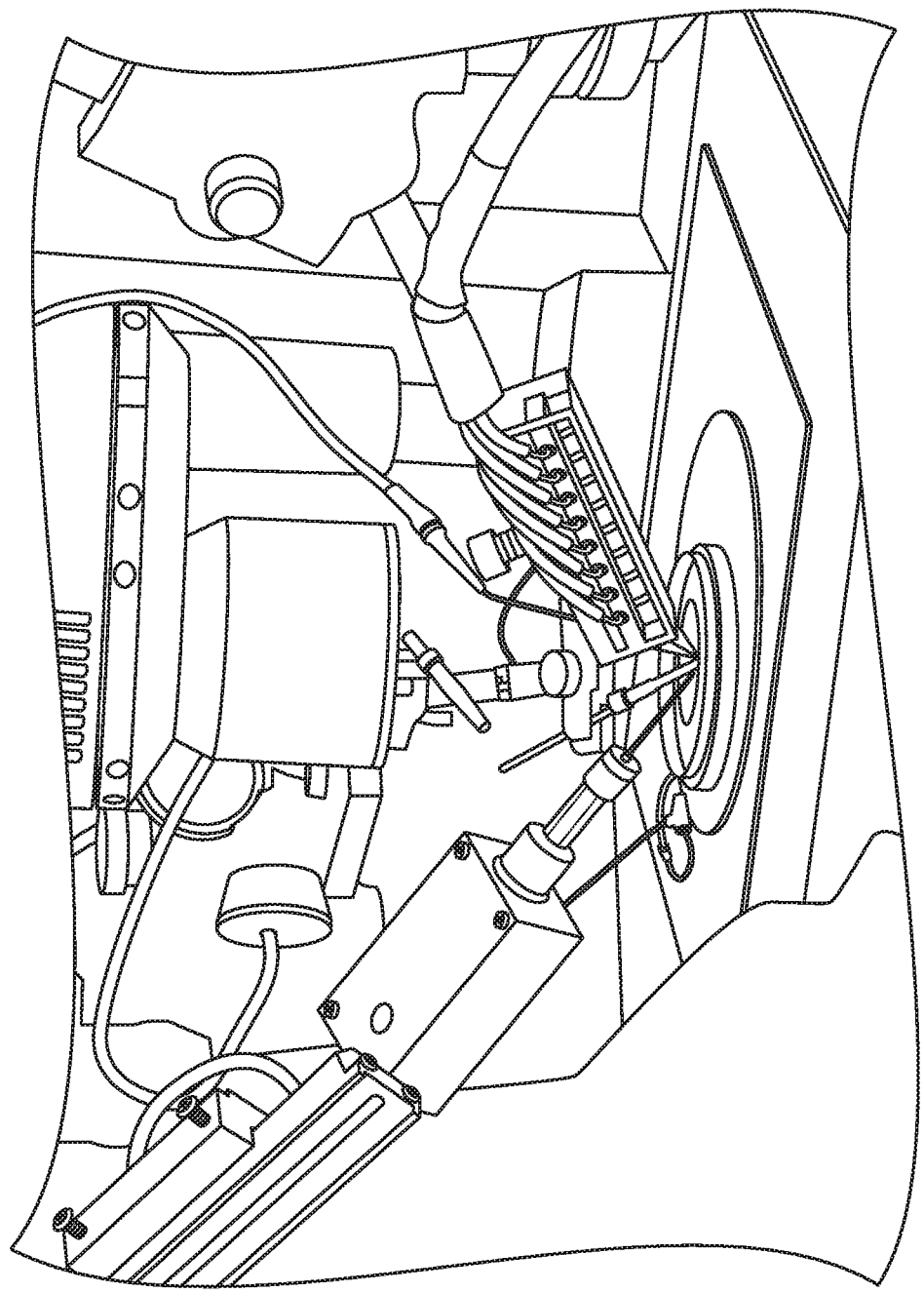
FIG. 20 is a photograph of an exemplary application in a typical electrophysiology setup for tissue slices, with an amplifier head-stage for intracellular recording, stimulation electrodes, and a microfluidic pipette for controlling solution environment according to an embodiment of the invention.
Figure 21:
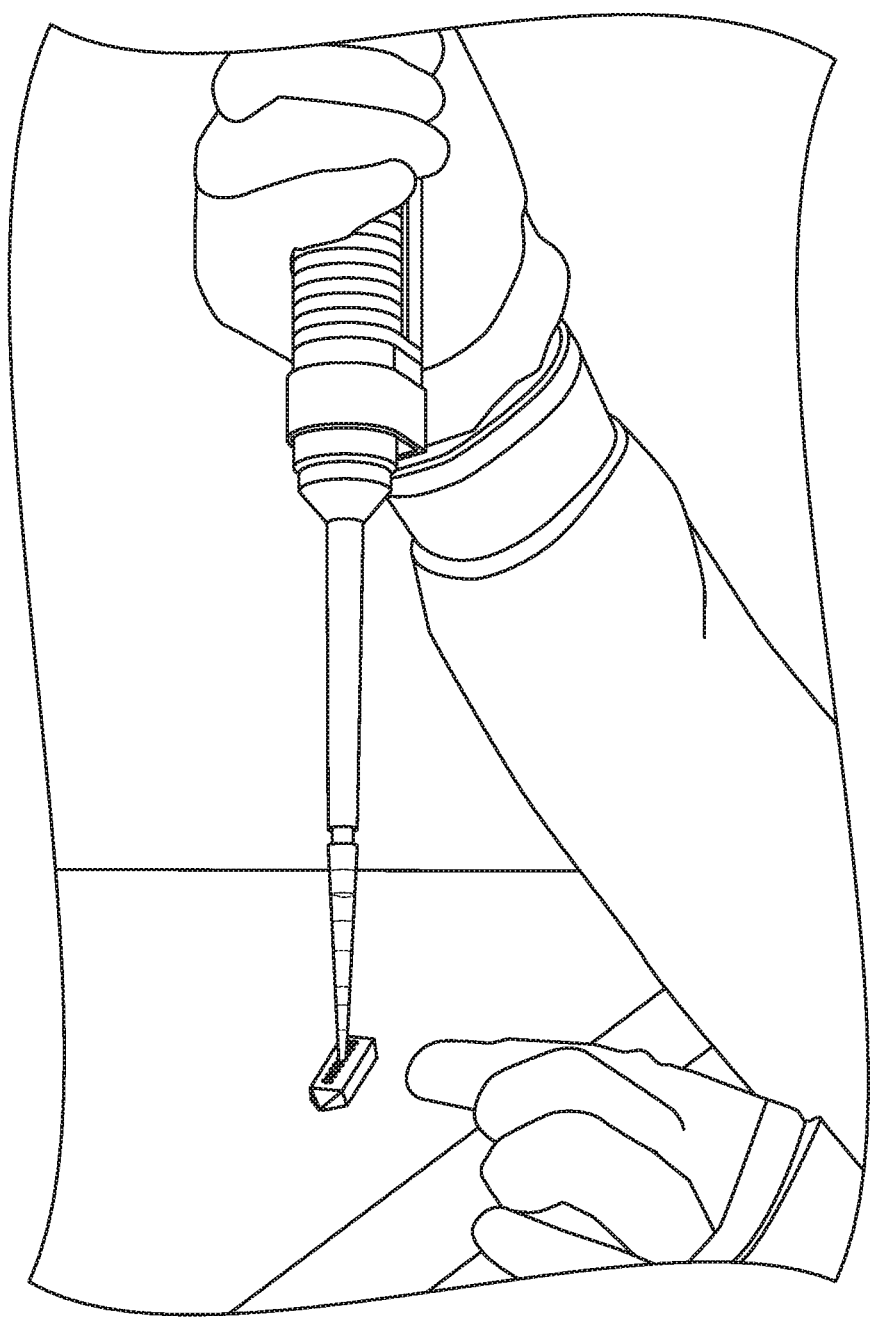
FIG. 21 is a photograph depicting the ease of filling of wells with a pipettor according to an embodiment of the inventionl Each well can store up to 35 uL of solution.

Another exemplary holding interface was fabricated in stainless-steel and is depicted in FIGS. 18A-18C. This interface is composed of three main parts: a bottom support 1802, a clamp 1803 and a manifold 1804. The bottom support 1802 houses a cavity for holding a microfluidic device 1801 in a fixed position, while the manifold 1804 allows individual pneumatic connectivity with each well. To address the pneumatic connections, the manifold 1804 contains flanges 1807, which are pressed against the elastomeric microfluidic device around the wells. The manifold 1804 is held against the microfluidic device via the clamp using a screw. The clamp connects with the bottom support and the manifold via the hinges 1805, 1806, ensuring a good sealing, even if there are slight variations in the height of the microfluidic device. The bottom support also has connected a cylindrical attachment arm 1809, which enables quick connection to laboratory micromanipulators. Pneumatic connections are achieved through 1 mm ID PVC tubing 1808. Additionally, the manifold contains interchangeable manifold ports, which are normally sealed with a screw 1810, but can be replaced with suitable contacts to form an electrical connection with well. FIG. 18C shows an exemplary contact, containing a spring loaded pin 1812, connected with a wire 1813 and insulated through the use of a Nylon screw 1811.

Microscopy Experiments

The setup was tested in experiments using an inverted fluorescence microscope (Leica DM IRB, with 10× and 40× objectives). In other experiments, a scanning confocal microscope (Leica IRE2) with confocal scanner (Leica TCS SP) and oil-immersion 40× objective (FIG. 10) was used.

A non-limiting means of micropositioning is the application of water hydraulic micromanipulators (Narishige MH-5, Japan) (1004, FIG. 10) or electrical micromanipulators (Scientifica PatchStar, UK), which allows 3D-positioning of the pipette, bringing the tip 1001 into proximity of the desired object of interest, which is in the open volume container 1006. The setup is suited to fit into a confined environment between objective 1008 and condenser lens assembly 1009.

Channel-Embedded Electrode Preparation

The introduction of electrodes into the chip was achieved by placing granules of Fields metal in to the well of the device, with subsequent heating on a hotplate to approximately 80 degrees, allowing the metal to melt into a pool. Pressure was applied to this well at 2 bar, reproducibly filling the channel within a few seconds. The device was then removed from the hotplate and allowed to cool to room temperature. Excess metal was removed from the tip of the device by agitation. Quality control was performed under a microscope and if cracks or voids were apparent, the device could be heated and reprocessed.

Flow Recirculation

In certain preferred embodiments, the simultaneous flow circulation device, for example as shown in FIGS. 22A-22E comprises at least two channels that are preferably aligned next to each other, where one channel preferably functions as a flow outlet, while another channel preferably functions as a flow inlet. Preferably, through the flow outlet, fluid is flowing from the channel into the open volume (outflow). Preferably, through the flow inlet, fluid is flowing from the open volume into the chip (inflow).

Figure 22A:
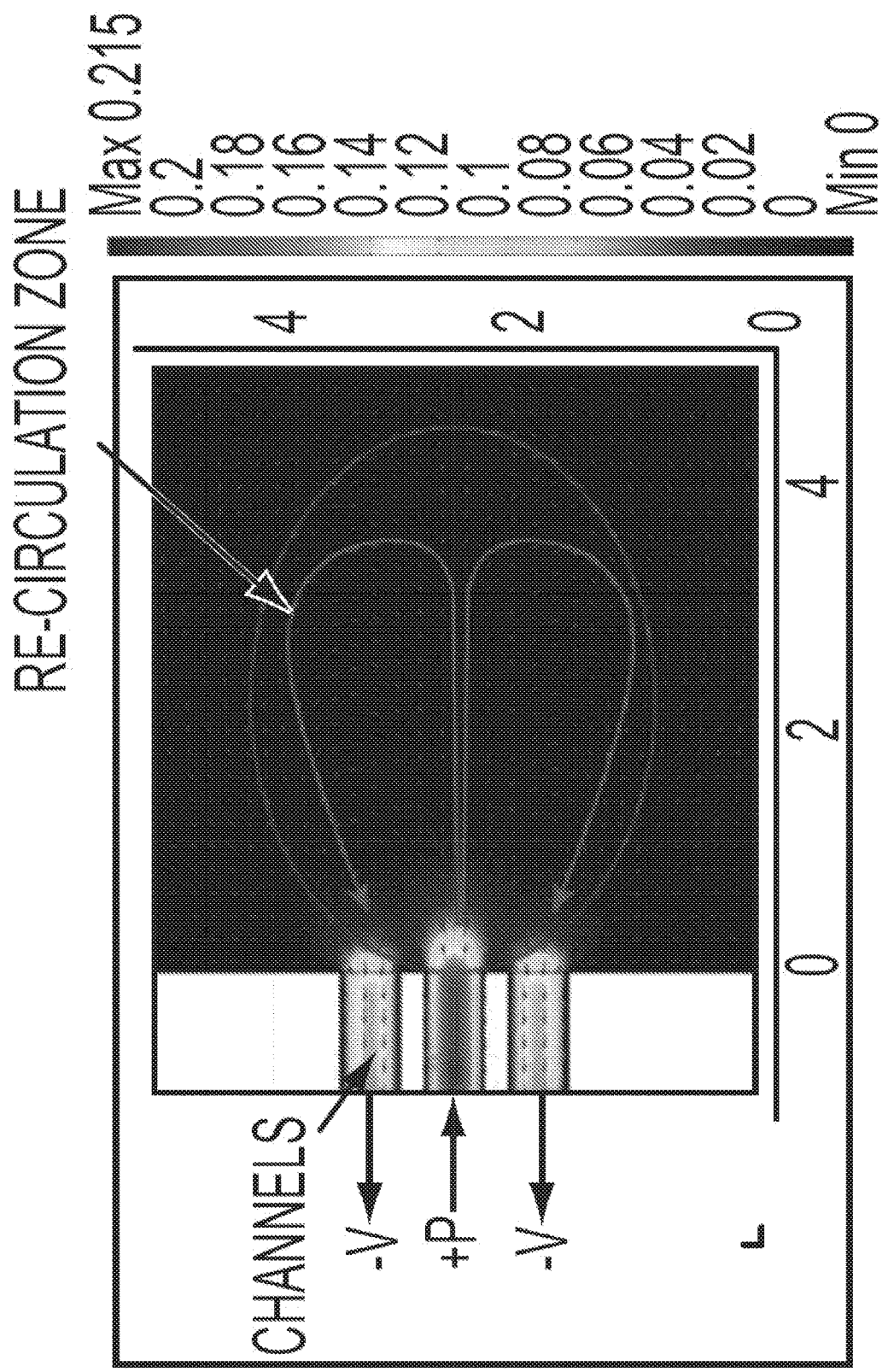
FIGS. 22A-22E show simultaneous flow re-circulation.
Figure 22B:
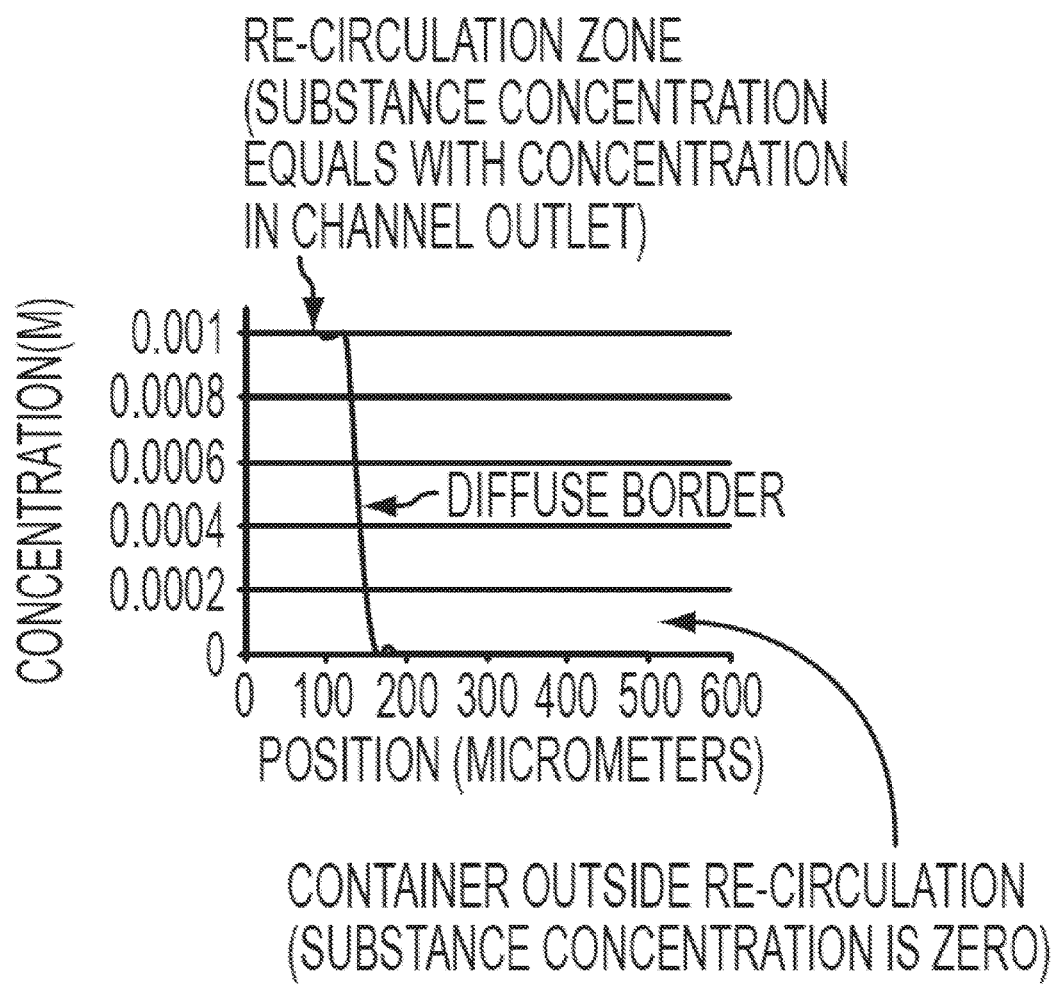

According to certain exemplary embodiments, if sufficient inflow is suitably maintained relative to outflow, a static flow circulation zone is formed (FIG. 22A). Preferably, apart from very small diffusion losses, all the fluid leaving the device is re-circulating into it. The volume of the re-circulation zone remains constant (static re-circulation zone). According to certain preferred embodiments of the present invention, the chemical composition inside the circulation zone corresponds to the composition of the outflow stream while the composition outside the circulation zone corresponds to composition of the open volume solution (FIG. 22B). Preferably, these two regions are separated by a diffusive layer. Diffusion losses result from loss of material from the recirculation zone by diffusion through the diffusion layer.

Figures 22C, 22D, 22E:
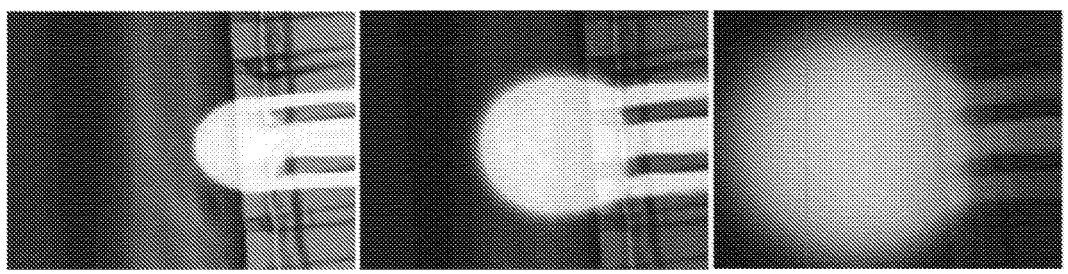

According to certain preferred embodiments of the present invention, the size of the circulation zone depends on the device layout, and on the inflow and outflow flow rates, respectively. Preferably, the size of the circulation zone can be adjusted during pipette operation by adjusting the inflow to outflow ratio (FIGS. 22C-22E). Further, the thickness of the diffusive layer depends on the diffusivity and flow rate in the circulation zone. Preferably, under stable operation conditions, the spatial distribution of substance concentration in the re-circulation zone can be suitably maintained over time (concentration distribution is time independent). Without circulation, the concentration distribution cannot be suitably maintained due to the diffusion that counteract with concentration gradients.

Additional Pipette Configurations

Referring now to FIG. 22C, various aspects of a microfluidic pipette 2500 are described. Pipette 2500 includes an substrate 2502 that defines a microfluidic outlet channel 2504 and two or more microfluidic inlet channels 2506a, 2506b.

As discussed herein, pipette 2500 can include additional channels. For example, the pipette 2500 can include a total of about 10 total outlet and inlet channels. In some embodiments, the number of inlet channels is greater than the number of outlet channels. For example, the ration of inlet to outlet channels can be 1:1, 2:1, 3:1, 4:1, 5:1 and the like.

Channels 2504 and 2506 can, in some embodiments, be parallel to each other as depicted. Channels 2504 and 2506 can have variety of cross-sectional profiles as discussed herein. In the embodiment depicted, channels 2504 and 2506 have square cross-sections with cross-sectional widths $wO$ and $wI$ and heights $hO$ and $hI$, respectively.

The openings of channels 2504 and 2506 can be positioned in a variety of locations on the dispensing region 2508. In some embodiments, the position of the channels 2504 and 2506 is defined with respect to a cross-sectional dimension of the channels 2504 and/or 2506.

In one embodiment, an inter-channel distance $dIC$ can be between about 1 about about 5 times a cross-sectional dimension of channels 2504 and/or 2506. For example, a ratio of $dIC$ to $wO$, $wI$, $hO$, and/or $hI$ can be selected from the group consisting of: between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, between about 4:1 and about 4.5:1, and between about 4.5:1 and about 5:1.

In another embodiments, a distance dB from the bottom of the openings to the bottom of the substrate 2502 can be between about 0.5 and about 5 times a cross-sectional dimension of channels 2504 and/or 2506. For example, a ratio of dB to $wO$, $wI$, $hO$, and/or $hI$ can be selected from the group consisting of: between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, between about 4:1 and about 4.5:1, and between about 4.5:1 and about 5:1.

Substrate 2502 can be selected from a variety of materials as discussed herein. In some embodiments, the substrate is an optically transparent material such as glass, polydimethylsiloxane (PDMS), poly(methyl methylacrylate) (PMMA), polyethylene (PE), and the like.

Figure 23A:
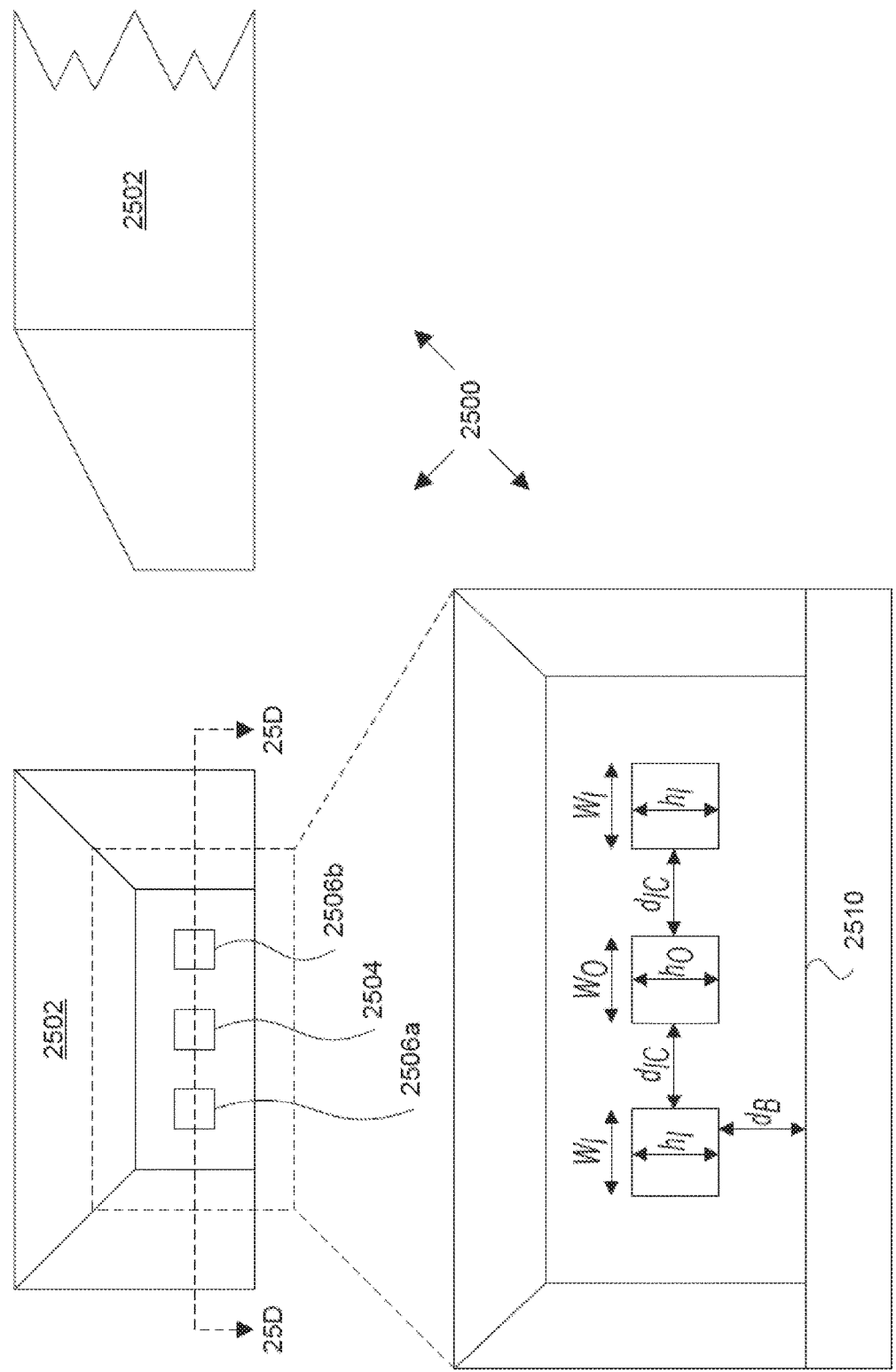
FIGS. 23A-23B depict a schematic of structure and operation of a microfluidic pipette according to one embodiment of the invention.
Figure 23B:
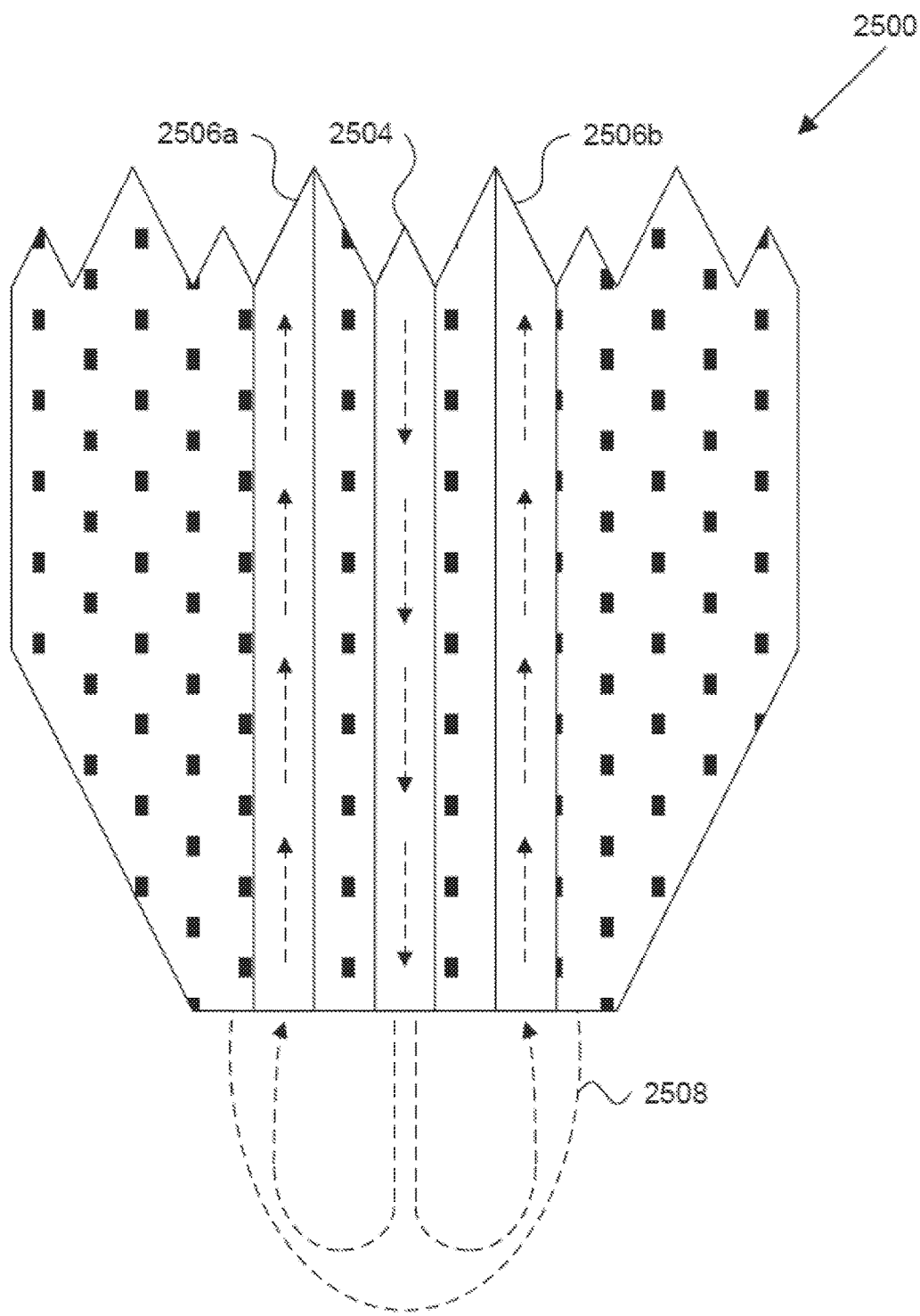

A dispensing region 2508 is located on the exterior of substrate 2502. Each of channels 2504 and 2506 include an opening on the dispensing region 2508. In operation, a fluid flows out of outlet channel 2504 and gathers and circulates in the dispensing region 2508 before being withdrawn by inlet channels 2506. An exemplary flow pattern is depicted in FIG. 23C.

As will be appreciated by one of ordinary skill in the art, the volume and dimensions of the fluid gathered in dispensing region 2508 will vary as a result of a variety of parameters including the ambient pressure in the open volume, the flow rates and pressures in channels 2504 and 2506, the fluid dispensed, the material of substrate 2502, and whether the dispensed fluid is in contact with another object (e.g., a cell). However, the dispensed fluid will often have have a generally circular to generally elliptical shape.

The length L of the dispensed liquid can, in some embodiments, be between about 1 and about 10 times the cross-sectional width w of one or more of channels 2504 and/or 2506. For example, the ratio W:w can be selected from the group consisting of between about 1:1 and about 2:1, between about 2:1 and about 3:1, between about 3:1 and about 4:1, between about 4:1 and about 5:1, between about 5:1 and about 6:1, between about 6:1 and about 7:1, between about 7:1 and about 8:1, between about 8:1 and about 9:1, and between about 9:1 and about 10:1.

The width W of the dispensed liquid can, in some embodiments, be between about 1 and about 6 times the cross-sectional width w of one or more channels 2504 and/or 2506. For example, the ratio W:w can be selected from the group consisting of between about 1:1 and about 2:1, between about 2:1 and about 3:1, between about 3:1 and about 4:1, between about 4:1 and about 5:1, and between about 5:1 and about 6:1.

The flow rate through channels 2504 and 2506 can be optimized to achieve a desired result. In general, lower flow rates impose less stress on cells. However, higher flows create a sharper concentration gradient, thereby increasing diffusion into the cell. In one exemplary embodiments having 10 μm square channels, flow rates ranging from 1 nl/second to 10 ml/second were achieved.

Channels 2504 and 2506 can interface with fluid source through a variety of means known to those of skill in the art including male/female connectors, tubing, wells, and the like.

The invention claimed is:

1. A system for applying a microfluidic device in microscopy, the system comprising:
 a microfluidic device having an elongated shape and defining two or more wells for solution storage and processing, the microfluidic device further including a tapered tip extending from the microfluidic device along its long axis and two or more channel exits on the tapered tip, the two or more channel exits separated from each other by an outer surface of the tapered tip, and including at least one outlet channel exit and at least one inlet channel exit; and
 an interface adapted and configured to:
 hold the microfluidic device in a freestanding manner; and
 facilitate simultaneous pneumatic connection of the two or more wells with external pressure and vacuum to generate a localized recirculating liquid flow path outside the pipette, wherein a liquid leaving the microfluidic device through the at least one outlet channel exit is withdrawn through the at least one inlet channel exit.

2. The system of claim 1, wherein the interface is coupled to a positioning device via an attachment arm, which has a cross-sectional dimension between about 5 mm and about 10 mm and a length between about 5 cm and about 20 cm.

3. The system of claim 1, wherein the microfluidic device is between about 6 mm and about 12 mm wide and about 3 mm and about 6 mm high and about 40 mm and about 150 mm long.

4. The system of claim 1, where the microfluidic device tip has a shape selected from the group consisting of: pyramidal, flat triangular, or flat rectangular.

5. The system of claim 1, wherein:
the microfluidic device is between about 6 mm and about 12 mm wide and about 3 mm and about 6 mm high and about 60 mm and about 100 mm long and is containing between 6 to 10 wells arranged in one row, where each well has volume between about 20 μL and 100 μL; and
the microfluidic device is held between at least two components, which are tightened around the device and which provides two or more individual pneumatic connection to two or more wells.

6. The system of claim 1, wherein the wells of the microfluidic device have a volume selected from the group consisting of: between about 10 μL and about 50 μL, about 50 μL and about 100 μL, and about 100 μL and about 500 μL.

7. The system of claim 1, wherein the microfluidic device has between 2 and 10 wells.

8. The system of claim 1, wherein the microfluidic device is a flow-recirculating microfluidic device, wherein total inflow through one or more channel exits is greater than total outflow through one or more channel exits and outflow stream is fully returned into inflow stream.

9. The system of claim 1, wherein the wells in the microfluidic chip are arranged in one row.

10. The system of claim 1, wherein the microfluidic device includes an integrated deformation damping well located between one or more wells and the microfluidic device tip.

11. The system of claim 1, wherein the interface is adapted and configured to provide electrical connectivity to the one or more wells.

12. The system of claim 1, wherein the microfluidic device is held between at least two components, which are tightened around the device by one or more selected from the group consisting of: a screw, an eccentric shaft, and one or more hooks or magnets.

13. The system of claim 1, wherein the microfluidic device is held against the interface by one or more selected from the group consisting of: an adhesion layer, magnets, and vacuum.

14. The system of claim 1, wherein each well is in individual communication with a pressure source.

15. The system of claim 1, wherein a pressure-tight seal is formed between the well of the microfluidic device and the interface, wherein the seal is formed in a situation selected from the group consisting of: when the interface is pressed against a soft surface of the microfluidic device by means of a flange on the interface; when the interface is pressed against a soft surface of the microfluidic device by means of a flange on the device; when the interface is pressed against a hard surface of the microfluidic device by means of a flange on the microfluidic device and a gasket; when the interface is pressed against a hard surface of the microfluidic device by means of a flange on a gasket; when the interface is pressed against a hard surface of the microfluidic device by means of a flange on a gasket, which extends into the well for sealing; and when the interface is pressed against the microfluidic device by means of an intermittent adhesion layer.

16. The system of claim 1, where the microfluidic device comprises:
a first portion defining the wells and microchannel grooves; and
a second portion adjacent to the first portion and sealing the microchannel grooves.

17. The system of claim 1, wherein the microfluidic device comprises:
a first portion defining microchannels; and
a second portion bonded to the first portion and further defining wells and supply channels, which are interfaced with the microchannels of the first portion.

18. The system of claim 1, wherein the interface includes one or more tubes adapted and configured to facilitate pneumatic connectivity with the one or more wells, through which the pressure in the wells can be controlled, wherein the tubes have an inner diameter between about 0.5 mm and about 2 mm.

19. The system of claim 1, wherein the microfluidic device includes one or more channel-embedded electrodes, and the interface is configured to provide electrical connectivity to the electrodes.

20. The system of claim 1, wherein the microfluidic device is fabricated from an elastomer and the system further comprises a support under the microfluidic device.

* * * * *